(12) United States Patent
Numazawa et al.

(10) Patent No.: US 8,722,288 B2
(45) Date of Patent: May 13, 2014

(54) DIPHENYLNAPHTHYLAMINE DERIVATIVES

(75) Inventors: Shigetaka Numazawa, Ibaraki (JP); Katsumi Abe, Fukushima (JP); Makoto Koike, Fukushima (JP); Kiyotaka Ihara, Yamaguchi (JP)

(73) Assignee: Hodogaya Chemical Co., Ltd., Tokyo (JP)

(*) Notice: Subject to any disclaimer, the term of this patent is extended or adjusted under 35 U.S.C. 154(b) by 0 days.

(21) Appl. No.: 13/503,227

(22) PCT Filed: Nov. 4, 2010

(86) PCT No.: PCT/JP2010/069623
§ 371 (c)(1),
(2), (4) Date: Apr. 20, 2012

(87) PCT Pub. No.: WO2011/055756
PCT Pub. Date: May 12, 2011

(65) Prior Publication Data
US 2012/0208117 A1    Aug. 16, 2012

(30) Foreign Application Priority Data

Nov. 6, 2009    (JP) ................................. 2009-254750

(51) Int. Cl.
*G03G 15/02*    (2006.01)
(52) U.S. Cl.
USPC ........................................ 430/58.85; 430/69
(58) Field of Classification Search
USPC ........... 430/58.05, 58.65, 58.7, 58.85, 72, 73, 430/69
See application file for complete search history.

(56) References Cited

U.S. PATENT DOCUMENTS 3,873,312 A    3/1975  Contois et al.
4,123,269 A    10/1978  Von Hoene et al.

(Continued)

FOREIGN PATENT DOCUMENTS

JP    54-150128    11/1979
JP    55-042380    10/1980

(Continued)

OTHER PUBLICATIONS

English Translations of JP-07020644A and JP-2008009070.*

(Continued)

*Primary Examiner* — Stewart Fraser
(74) *Attorney, Agent, or Firm* — Greenblum & Bernstein, P.L.C.

(57) ABSTRACT

[Problems] To provide a novel compound which has a high carrier mobility and is useful as a charge-transporting agent that is not only capable of stably forming a photosensitive layer without precipitating crystals or forming pinholes at the time of forming the photosensitive layer but is also capable of forming an organic photosensitive material for electrophotography that has a high sensitivity and a low residual potential.
[Means for Solution] A diphenylnaphthylamine derivative represented by the following general formula (1),

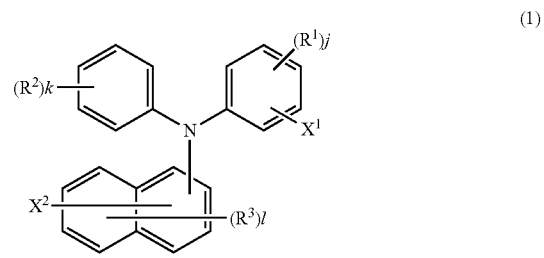

wherein $R^1$ to $R^3$ are alkyl groups, k is an integer of 0 to 3, j is an integer of 0 to 4, l is an integer of 0 to 6, and $X^1$ and $X^2$ are hydrocarbon groups having at least one ethylenically unsaturated bond.

4 Claims, 2 Drawing Sheets

(56) References Cited

U.S. PATENT DOCUMENTS

| | | |
|---|---|---|
| 4,150,987 A | 4/1979 | Anderson et al. |
| 4,278,747 A | 7/1981 | Murayama et al. |
| 4,367,273 A | 1/1983 | Murayama et al. |
| 4,423,129 A | 12/1983 | Takasu et al. |
| 4,751,163 A | 6/1988 | Hagiwara et al. |
| 5,213,924 A | 5/1993 | Sakamoto |
| 5,283,142 A | 2/1994 | Mayama et al. |
| 5,334,470 A | 8/1994 | Shimada et al. |
| 5,436,100 A | 7/1995 | Shimada et al. |
| 5,475,137 A | 12/1995 | Shimada et al. |
| 7,563,548 B2 | 7/2009 | Kondoh et al. |
| 2003/0111692 A1 | 6/2003 | Toguchi et al. |
| 2007/0207395 A1* | 9/2007 | Kondoh et al. ............ 430/58.85 |
| 2012/0052427 A1 | 3/2012 | Numazawa et al. |

FOREIGN PATENT DOCUMENTS

| | | |
|---|---|---|
| JP | 57-101844 | 6/1982 |
| JP | 58-032372 | 7/1983 |
| JP | 61-023154 | 1/1986 |
| JP | 1-142642 | 6/1989 |
| JP | 4-179961 | 6/1992 |
| JP | 4-066023 | 10/1992 |
| JP | 5-019701 | 3/1993 |
| JP | 5-088389 | 4/1993 |
| JP | 5-088398 | 4/1993 |
| JP | 6-214412 | 8/1994 |
| JP | 6-222581 | 8/1994 |
| JP | 07020644 A * | 1/1995 |
| JP | 7-021646 | 3/1995 |
| JP | 7-175236 | 7/1995 |
| JP | 11-065136 | 3/1999 |
| JP | 11-102784 | 4/1999 |
| JP | 2004-317591 | 11/2004 |
| JP | 2005-162641 | 6/2005 |
| JP | 2005-206507 | 8/2005 |
| JP | 2007-169190 | 7/2007 |
| JP | 2007-169205 | 7/2007 |
| JP | 2008009070 A * | 1/2008 |

OTHER PUBLICATIONS

Search report from International Application No. PCT/JP2010/069623, mail date is Dec. 28, 2010.

Extended European Search Report issued with respect to European Application No. 10828316.9, dated Mar. 1, 2013.

* cited by examiner

DIPHENYLNAPHTHYLAMINE DERIVATIVES

TECHNICAL FIELD

This invention relates to diphenylnaphthylamine derivatives which have high carrier mobility and are useful as a charge-transporting agent for photosensitive materials for electrophotography.

BACKGROUND ART

As inorganic photoconductive materials, there have been known amorphous silicon, amorphous selenium, cadmium sulfide, zinc oxide and the like. Inorganic photosensitive materials formed by using such inorganic photoconductive materials have heretofore been widely used in the field of electrophotography. However, selenium and cadmium sulfide are toxic and must be recovered, selenium has poor heat resistance since it is crystallized upon being heated, cadmium sulfide and zinc oxide have poor humidity resistance, and zinc oxide, further, has no print endurance. In recent years, therefore, it is becoming a main stream to use an organic photosensitive material comprising an electrically conducting substrate, and formed thereon, an organic photosensitive layer that contains a charge-generating agent and a charge-transporting agent as a photoconductive material.

As the organic photosensitive material, there has been known the one of the single-layer type in which the photosensitive layer formed on the electrically conducting substrate contains a charge-generating agent and a charge-transporting agent that are dispersed in a resin binder, and the one of the lamination type in which the photosensitive layer includes a charge-generating layer containing the charge-generating agent dispersed in the resin binder and a charge-transporting layer containing the charge-transporting agent dispersed in the resin binder. The organic photosensitive material of either type has such advantages as small weight compared to the inorganic photosensitive material and permitting the photosensitive layer to be easily formed, as well as little affecting the environment.

In the above organic photosensitive material for electrophotography, the charge-transporting agent must have such properties as efficiently receiving carriers (positive charge or negative charge) generated by the charge-generating agent upon the irradiation with light, quickly moving the carriers in the photosensitive layer, and quickly extinguishing the electric charge on the surface of the photosensitive layer when an electric field is applied thereto. The rate at which the carriers move per a unit electric field is called carrier mobility. A high carrier mobility means that the carriers quickly move in the photosensitive layer (or in the charge-transporting layer). The carrier mobility is specific to a compound used as the charge-transporting agent and, therefore, a compound having a high carrier mobility must be used as the charge-transporting agent.

The charge-transporting agent and the charge-generating agent are dissolved in an organic solvent together with a resin binder being applied, followed by drying (removal of the solvent) to thereby form the photosensitive layer. Therefore, the charge-transporting agent must, further, have a property to form a homogeneous photosensitive layer without precipitating crystals or without forming pinholes. If the photosensitive layer contains portions where crystals are precipitating or pinholes are forming, dielectric breakdown occurs at such portions. When an image is formed by the electrophotography, therefore, image defects may occur.

As described above, the charge-transporting agent must satisfy various properties, and a variety of compounds have hitherto been proposed as the charge-transporting agents (see patent documents 1 to 14).

PRIOR ART DOCUMENTS

Patent Documents

Patent document 1: JP-B-58-032372
Patent document 2: JP-A-1-142642
Patent document 3: JP-A-5-088389
Patent document 4: JP-B-7-021646
Patent document 5: JP-B-5-019701
Patent document 6: JP-B-55-042380
Patent document 7: JP-A-57-101844
Patent document 8: JP-A-54-150128
Patent document 9: JP-A-61-023154
Patent Document 13: U.S. Pat. No. 3,873,312
Patent document 14: JP-B-4-066023

OUTLINE OF THE INVENTION

Problems that the Invention is to Solve

When the photosensitive layers are formed by forming the charge-generating layer and the charge-transporting layer in combination, however, only few of many compounds proposed by the above patent documents as charge-transporting agents can satisfy the properties and conditions practically required for the photosensitive material. Namely, many problems are waiting to be overcome, such as crystals precipitate after the film is formed, the surface potential is not sufficiently maintained when dark despite the film is formed, the surface potential cannot be sufficiently attenuated after having been irradiated with light (low sensitivity, high residual potential) and so on.

It is, therefore, an object of the present invention is to provide a novel and useful compound as a charge-transporting agent which has a high carrier mobility, which is capable of stably forming a photosensitive layer without precipitating crystals or forming pinholes at the time of forming the photosensitive layer, and which is capable of forming an organic photosensitive material for electrophotography having a high sensitivity and a low residual potential.

Another object of the invention is to provide a charge transporting agent comprising the above compound and an organic photosensitive material for electrophotography that contains the charge-transporting agent in the photosensitive layer.

Means for Solving the Problems

According to the present invention, there is provided a diphenylnaphthylamine derivative represented by the following general formula (1),

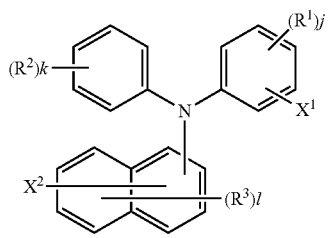

(1)

wherein, j is an integer of 0 to 4,
k is an integer of 0 to 5,
l is an integer of 0 to 6,
$R^1$, $R^2$ and $R^3$ may be the same or different, and are groups selected from the group consisting of alkyl group having 1 to 6 carbon atoms; alkoxy group having 1 to 6 carbon atoms; halogen atom; aromatic hydrocarbon group; condensed polycyclic aromatic group; aromatic heterocyclic group; and disubstituted amino group having, as substituents, alkyl groups having 1 to 6 carbon atoms, alkenyl groups having 2 to 6 carbon atoms, aralkyl groups, aromatic hydrocarbon groups or aromatic heterocyclic groups; and
when $R^1$, $R^2$ and $R^3$ are present in plural numbers, the plurality of $R^1$, $R^2$ and $R^3$ may be each the same or different, and may be bonded together to form a ring structure,
$X^1$ is a monovalent group represented by the following general formula (1a),

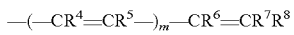

(1a)

wherein, m is 0 or 1,
$R^4$ to $R^8$ may be the same or different, and are hydrogen atoms, alkyl groups having 1 to 6 carbon atoms, alkoxy groups having 1 to 6 carbon atoms, aromatic hydrocarbon groups, condensed polycyclic aromatic groups or aromatic heterocyclic groups, $R^7$ and $R^8$ together may form a ring and when $R^7$ is a hydrogen atom or an alkyl group, $R^8$ is an aromatic hydrocarbon group, a condensed polycyclic aromatic group or an aromatic heterocyclic group, and
$X^2$ is a monovalent group represented by the following general formula (1b),

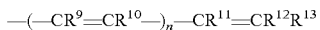

(1b)

wherein, n is 0 or 1,
$R^9$ to $R^{13}$ may be the same or different, and are hydrogen atoms, alkyl groups having 1 to 6 carbon atoms, alkoxy groups having 1 to 6 carbon atoms, aromatic hydrocarbon groups, condensed polycyclic aromatic groups or aromatic heterocyclic groups, $R^{12}$ and $R^{13}$ together may form a ring and when $R^{12}$ is a hydrogen atom or an alkyl group, $R^{13}$ is an aromatic hydrocarbon group, a condensed polycyclic aromatic group or an aromatic heterocyclic group.

According to the invention, it is desired that the diphenylnaphthylamine derivative has a structure represented by the following general formula (1') from the standpoint of properties as a charge-transporting agent.

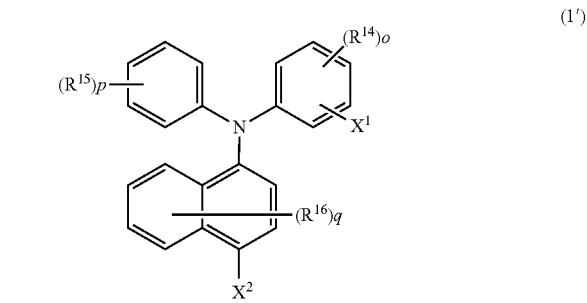

(1')

wherein, o is a number corresponding to j in the above general formula (1), and is an integer of 0 to 4, p is a number corresponding to k in the above general formula (1), and is an integer of 0 to 5, q is a number corresponding to l in the above general formula (1), and is an integer of 0 to 6, $R^{14}$, $R^{15}$ and $R^{16}$ are, respectively, groups corresponding to $R^1$, $R^2$ and $R^3$ in the above general formula (1), $X^1$ is a monovalent group represented by the above general formula (1a), and $X^2$ is a monovalent group represented by the above general formula (1b).

According to the invention, further, it is desired that the diphenylnaphthylamine derivative is the one represented by the following general formula (1") or the general formula (1''') among those represented by the above general formula (1').

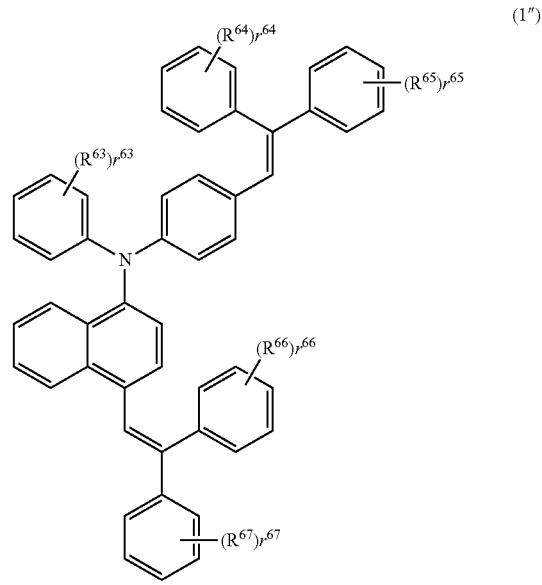

(1")

-continued

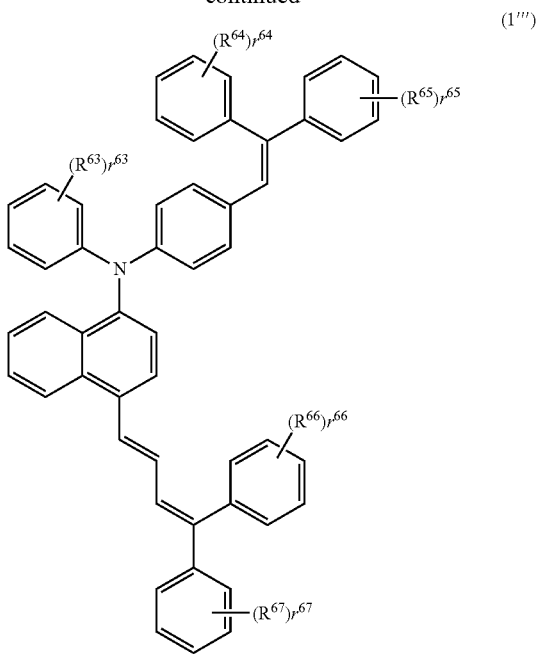

(1'''')

In the above general formula (1'') or (1'''), $r^{63}$ to $r^{67}$ may be the same or different, and are integers of 0 to 5, $R^{63}$ to $R^{67}$ may be the same or different, and are groups selected from the group consisting of alkyl group having 1 to 6 carbon atoms; alkoxy group having 1 to 6 carbon atoms; halogen atom; aromatic hydrocarbon group; condensed polycyclic aromatic group; aromatic heterocyclic group; and disubstituted amino group having, as substituents, alkyl groups having 1 to 6 carbon atoms, alkenyl groups having 2 to 6 carbon atoms, aralkyl groups, aromatic hydrocarbon groups or aromatic heterocyclic groups; and when $R^{63}$, $R^{64}$, $R^{65}$, $R^{66}$ and $R^{67}$ are present in plural numbers, the plurality of $R^{63}$, $R^{64}$, $R^{65}$, $R^{66}$ and $R^{67}$ may be each the same or different, and may be bonded together to form a ring structure, According to the present invention, further, there is provided a charge-transporting agent comprising the diphenylnaphthylamine derivative.

According to the present invention, there is further provided an organic photosensitive material for electrophotography having an organic photosensitive layer formed on an electrically conducting substrate, wherein the organic photosensitive layer contains the diphenylnaphthylamine derivative as a charge-transporting agent.

In the organic photosensitive material for electrophotography of the present invention, it is desired that:

(A) The organic photosensitive layer is a lamination type photosensitive layer comprising a charge-generating layer that contains the charge-generating agent dispersed in a resin binder and a charge-transporting layer that contains the charge-transporting agent dispersed in a resin binder; and (B) The organic photosensitive layer is a single photosensitive layer containing the charge-generating agent and the charge-transporting agent dispersed in a resin binder.

Effects of the Invention

The diphenylnaphthylamine derivative represented by the above general formula (1) of the invention is a novel compound, has a high carrier mobility, and is very useful as a charge-transporting agent which is used for the production of an organic photosensitive material for electrophotography.

Besides, the organic photosensitive material containing the above diphenylnaphthylamine derivative as the charge-transporting agent does not cause the precipitation of crystals or the formation of pinholes at the time of forming the photosensitive layer (forming the film). Moreover, the organic photosensitive material containing the diphenylnaphthylamine derivative is highly sensitive and has a low residual potential. The organic photosensitive material permits the surface potential to fluctuate little, permits the sensitivity to decrease little and permits the residual potential to accumulate little even after the image is repetitively formed by the electrophotography, i.e. features excellent durability.

MODES FOR CARRYING OUT THE INVENTION

<Diphenylnaphthylamine Derivatives>

Figure 1:
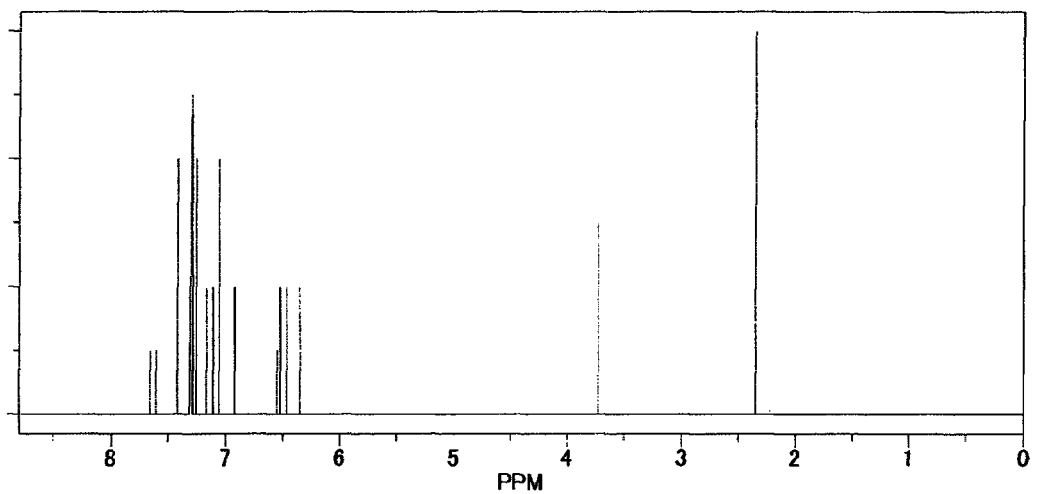
[FIG. 1] shows an NMR spectrum of a compound of Example 1 (Example Compound 25).

The diphenylnaphthylamine derivatives of the present invention are represented by the following general formula (1),

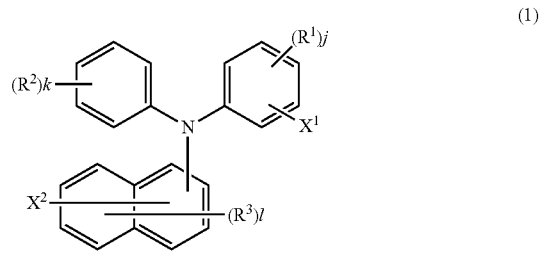

(1)

In the above general formula (1), j represents the number of the groups $R^1$ and is an integer of 0 to 4, k represents the number of the groups $R^2$ and is an integer of 0 to 5, and l represents the number of the groups $R^3$ and is an integer of 0 to 6.

Further, the groups $R^1$ to $R^3$ and the groups $X^1$ and $X^2$ are as described below.

(Groups $R^1$ to $R^3$)

The groups $R^1$ to $R^3$ may be the same or different, and are any of alkyl groups, alkoxy groups, halogen atoms, aromatic hydrocarbon groups, condensed polycyclic aromatic groups, aromatic heterocyclic groups or disubstituted amino groups.

The alkyl group has 1 to 6 carbon atoms, and may be of the form of a straight chain or of a branched form.

Concrete examples of the alkyl group include methyl group, ethyl group, propyl group, butyl group, hexyl group, tert-butyl group and isopropyl group.

The alkoxy group has 1 to 6 carbon atoms, and may be of the form of a straight chain or of a branched form.

Concrete examples of the alkoxy group include methoxy group, ethoxy group and propoxy group.

As the halogen atom, there can be exemplified fluorine atom, chlorine atom, bromine atom and iodine atom.

As the aromatic hydrocarbon group or the condensed polycyclic aromatic group, there can be exemplified phenyl group, naphthyl group, anthryl group and pyrenyl group.

As the aromatic heterocyclic group, there can be exemplified pyridyl group, pyrrolyl group, thienyl group, furyl group, carbazolyl group and pyronyl group.

The disubstituted amino group has two substituents bonded to the nitrogen atom thereof. Here, the substituents are selected from the group consisting of alkyl group (either straight chain or branched) having 1 to 6 carbon atoms, alkenyl group (either straight chain or branched, e.g., allyl group) having 2 to 6 carbon atoms, aralkyl group (e.g., benzyl group or phenetyl group), aromatic hydrocarbon group and aromatic heterocyclic group. Among them, concrete examples of the alkyl group, aromatic hydrocarbon group and aromatic heterocyclic group are those exemplified above.

As the disubstituted amino group having the above substituents, there can be exemplified dialkylamino groups such as dimethylamino group and diethylamino group; diarylamino groups such as diphenylamino group and dinaphthylamino group; diaralkylamino groups such as dibenzylamono group and diphenetylamino group; diheteroarylamino groups such as dipyridylamino group and dithienylamino group; and dialkenylamino groups such as diallylamino group and the like.

When the groups $R^1$, $R^2$ and $R^3$ are present in plural numbers (when j, k and l are integers of 2 or more), the groups $R^1$, $R^2$ and $R^3$ present in plural numbers may be different from each other, or may be bonded together to form rings.

The above alkyl group, alkoxy group, aromatic hydrocarbon group, condensed polycyclic aromatic group and aromatic heterocyclic group may have a substituent. Further, the substituents possessed by the disubstituted amino group may have another substituent.

As the another substituent, there can be exemplified the following groups provided they satisfy the conditions of predetermined numbers of carbon atoms.

Hydroxyl group;

halogen atoms such as fluorine atom, chlorine atom, bromine atom and iodine atom;

alkyl groups (either straight chain or branched form) having 1 to 6 carbon atoms, such as methyl group, ethyl group, propyl group, butyl group, hexyl group and isopropyl group;

alkoxy groups having 1 to 6 carbon atoms, such as methoxy group, ethoxy group and propoxy group;

alkenyl groups such as allyl group;

aralkyl groups such as benzyl group, naphthylmethyl group and phenetyl group;

aryloxy groups such as phenoxy group and tolyloxy group;

arylalkoxy groups such as benzyloxy group and phenetyloxy group;

aromatic hydrocarbon groups or condensed polycyclic aromatic groups such as phenyl group, naphthyl group, anthryl group and pyrenyl group;

aromatic heterocyclic groups such as pyridyl group, pyrrolyl group, thienyl group, furyl group, carbazolyl group and pyronyl group;

arylvinyl groups such as styryl group and naphthylvinyl group; and acyl groups such as acetyl group and benzoyl group.

When the above exemplified substituents are present in plural numbers, these substituents may be condensed with each other to form carbocyclic groups or heterocyclic groups (oxygen atom, sulfur atom, nitrogen atom or the like atom may be included as hetero atom) through a single bond or through a divalent group such as methylene group, ethylen group, carbonyl group, vinylidene group or ethylenylene group. These substituents may, further, have another substituent.

The above groups $R^1$, $R^2$ and $R^3$ are, particularly preferably, methyl groups or phenyl groups.

(Group $X^1$)

In the general formula (1), further, the group $X^1$ is a monovalent group represented by the following formula (1a),

$$-(-CR^4=CR^5-)_m-CR^6=CR^7R^8 \quad (1a)$$

wherein m is a number of the recurring unit $(-CR^4=CR^5-)$, and is 0 or 1.

In the formula (1a), $R^4$ to $R^8$ may be the same or different, and are hydrogen atoms, straight-chain or branched alkyl groups having 1 to 6 carbon atoms, straight-chain or branched alkoxy groups having 1 to 6 carbon atoms, aromatic hydrocarbon groups, condensed polycyclic aromatic groups or aromatic heterocyclic groups. Concrete examples of the groups $R^4$ to $R^8$ may be the same as those exemplified as the groups $R^1$ to $R^3$. These groups $R^4$ to $R^8$, too, may have the same substituents as those of the groups $R^1$ to $R^3$.

Of the groups $R^4$ to $R^8$, when $R^7$ is a hydrogen atom or an alkyl group, $R^8$ is an aromatic hydrocarbon group, a condensed polycyclic aromatic group or a heterocyclic group.

These groups $R^7$ and $R^8$ together may form a ring. For example, $R^7$ and $R^8$ may be bonded together directly or via methylene group, ethylene group, carbonyl group, vinylidene group or ethylenylene group to form a carbocyclic group or a hetrocyclic group that contains oxygen atom, sulfur atom or nitrogen atom.

(Group $X^2$)

In the general formula (1), the group $X^2$ is a monovalent group represented by the following formula (1b),

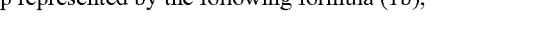

$$-(-CR^9=CR^{10}-)_n-CR^{11}=CR^{12}R^{13} \quad (1b)$$

In the general formula (1b), n is a number of the recurring unit $(-CR^9=CR^{10}-)$, and is 0 or 1.

In the above formula, $R^9$ to $R^{13}$ may be the same or different, and are hydrogen atoms, straight-chain or branched alkyl groups having 1 to 6 carbon atoms, straight-chain or branched alkoxy groups having 1 to 6 carbon atoms, aromatic hydrocarbon groups, condensed polycyclic aromatic groups or aromatic heterocyclic groups.

Concrete examples of the groups $R^9$ to $R^{13}$ may be the same as those exemplified as the groups $R^1$ to $R^3$.

That is, as the alkyl group having 1 to 6 carbon atoms, there can be exemplified methyl group, ethyl group, propyl group, butyl group, hexyl group, tert-butyl group and isopropyl group.

As the alkoxy group having 1 to 6 carbon atoms, there can be exemplified methoxy group, ethoxy group and propyloxy group.

As the aromatic hydrocarbon group or condensed polycyclic aromatic group, there can be exemplified phenyl group, naphthyl group, anthracenyl group and pyrenyl group.

As the aromatic heterocyclic group, there can be exemplified pyridyl group, pyrrolyl group, thienyl group, furyl group, carbazolyl group and pyronyl group.

Further, the groups $R^9$ to $R^{13}$, too, may have the same substituent as those of the groups $R^1$ to $R^3$.

Of the groups $R^9$ to $R^{13}$, when $R^{12}$ is a hydrogen atom or an alkyl group, $R^{13}$ is an aromatic hydrocarbon group, a condensed polycyclic aromatic group or a heterocyclic group.

Among these groups, further, the groups $R^{12}$ and $R^{13}$ together may form a ring like the above groups $R^7$ and $R^8$. For example, $R^{12}$ and $R^{13}$ may be bonded together directly or via methylene group, ethylene group, carbonyl group, vinylidene group or ethylenylene group to form a carbocyclic group or a hetrocyclic group that contains oxygen atom, sulfur atom or nitrogen atom.

Described below are typical examples of the diphenyl-naphthylamine derivative represented by the above general formula (1) to which only, however, the invention is in no way limited.

(Example compound 1)

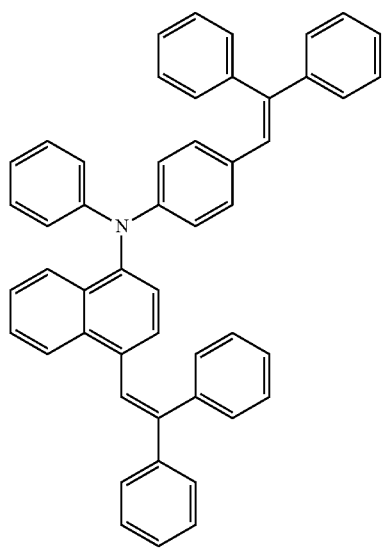

(Example compound 2)

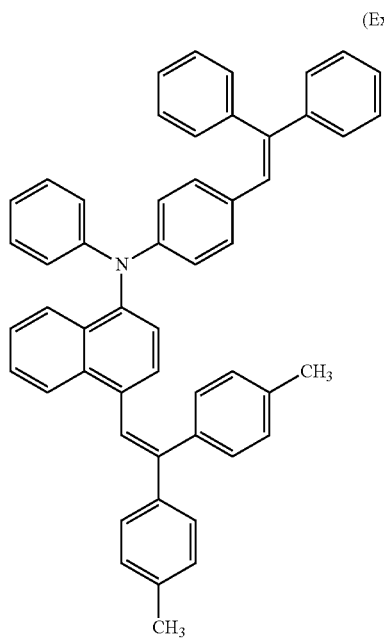

(Example compound 3)

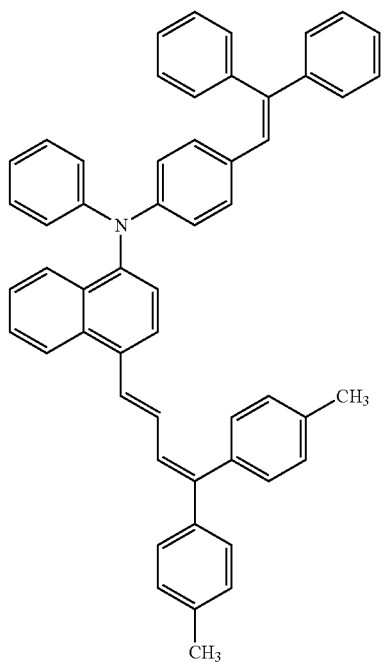

(Example compound 4)

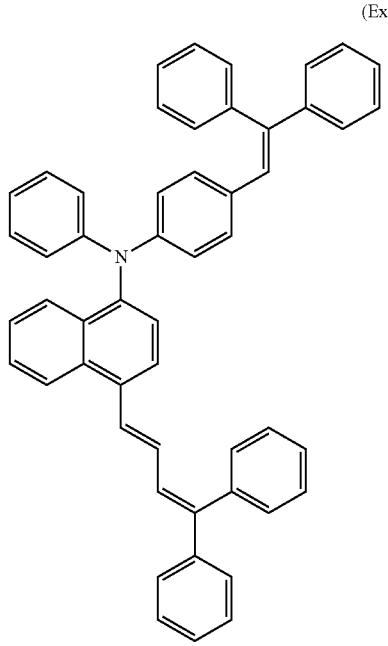

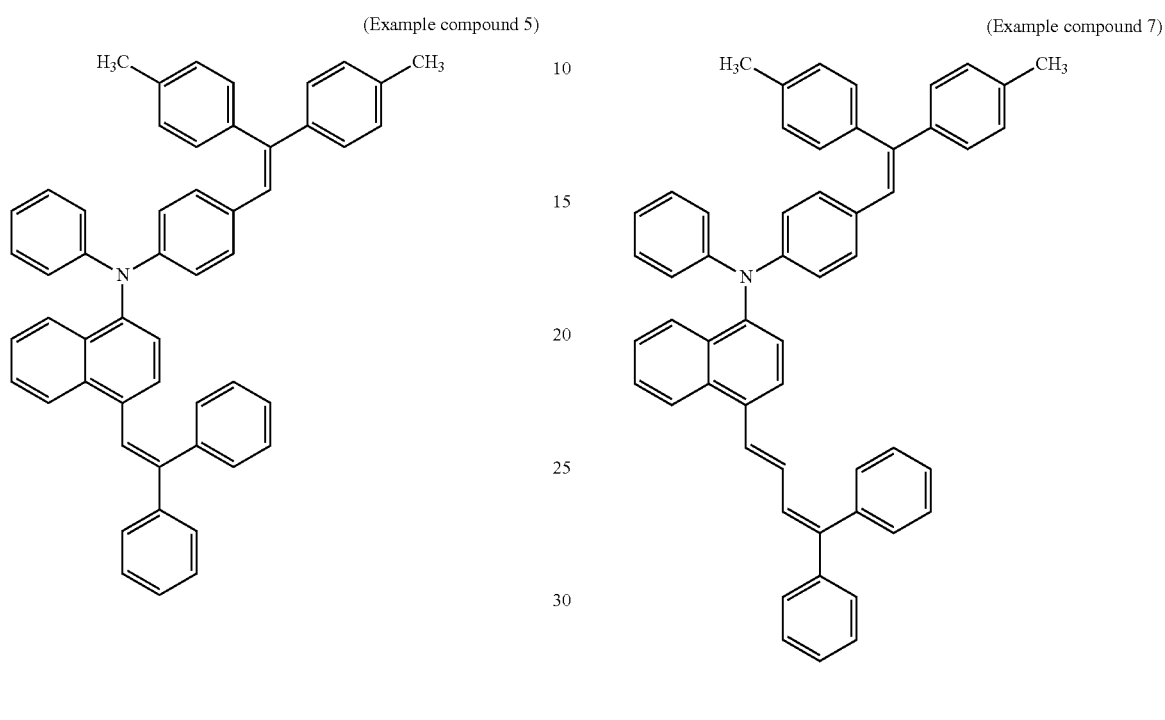
(Example compound 5)
(Example compound 7)
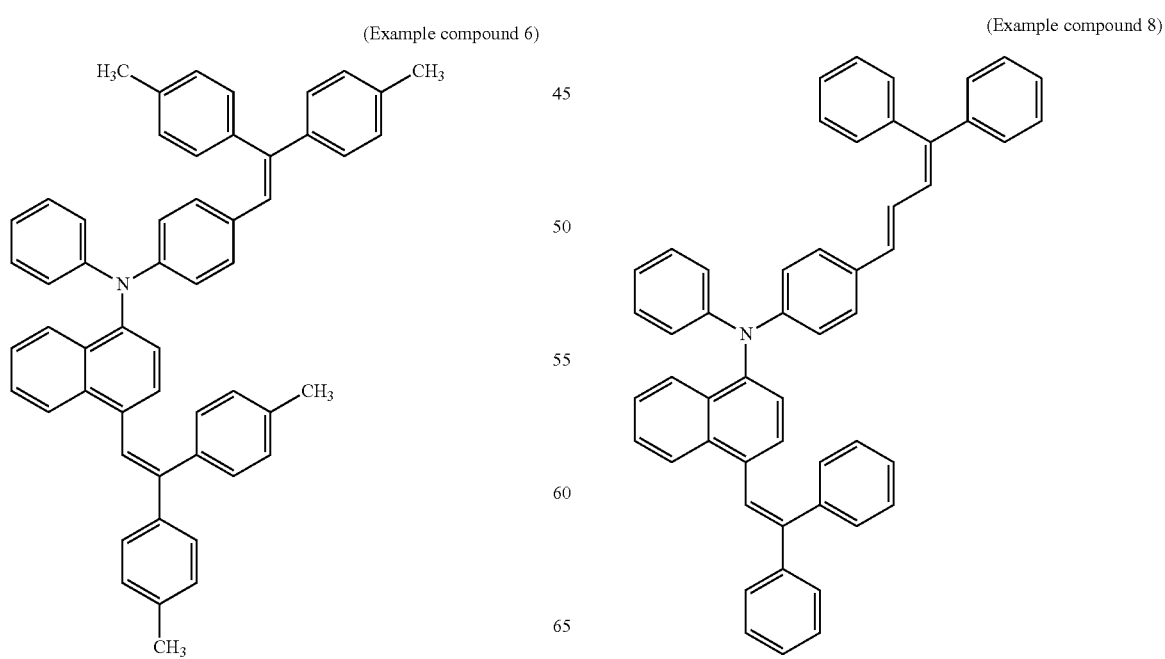
(Example compound 6)
(Example compound 8)

(Example compound 9)
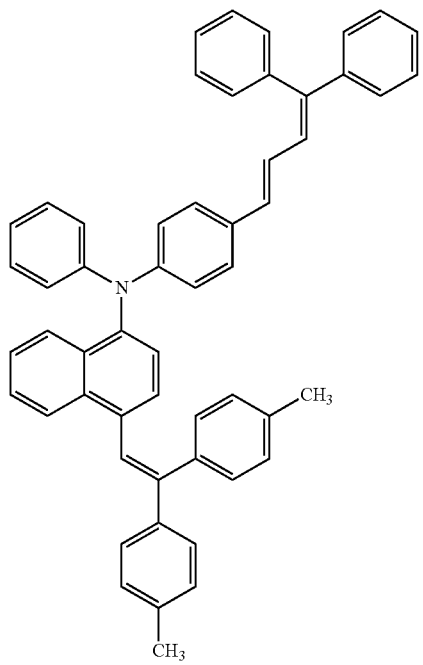
(Example compound 10)
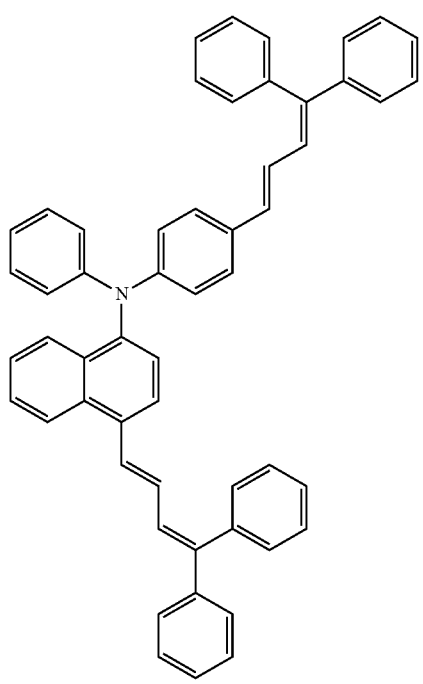
(Example compound 11)
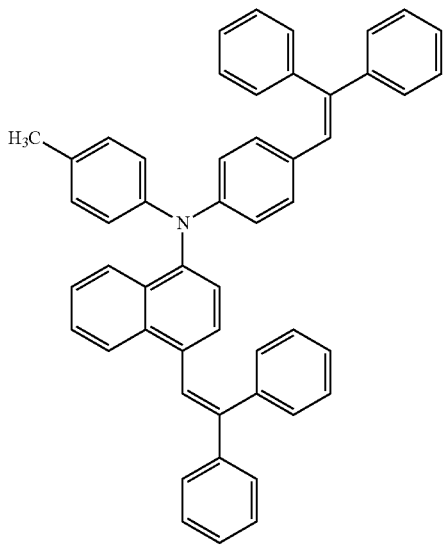
(Example compound 12)
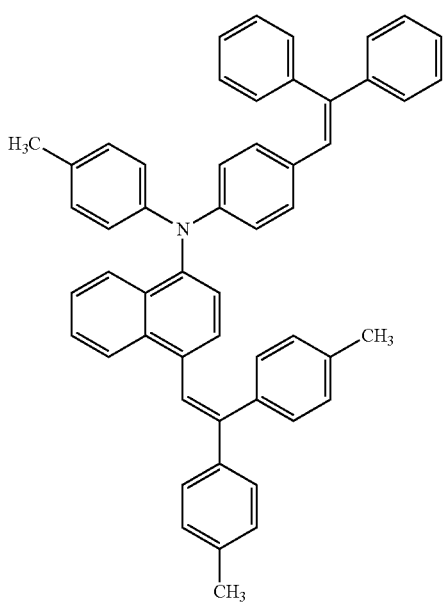

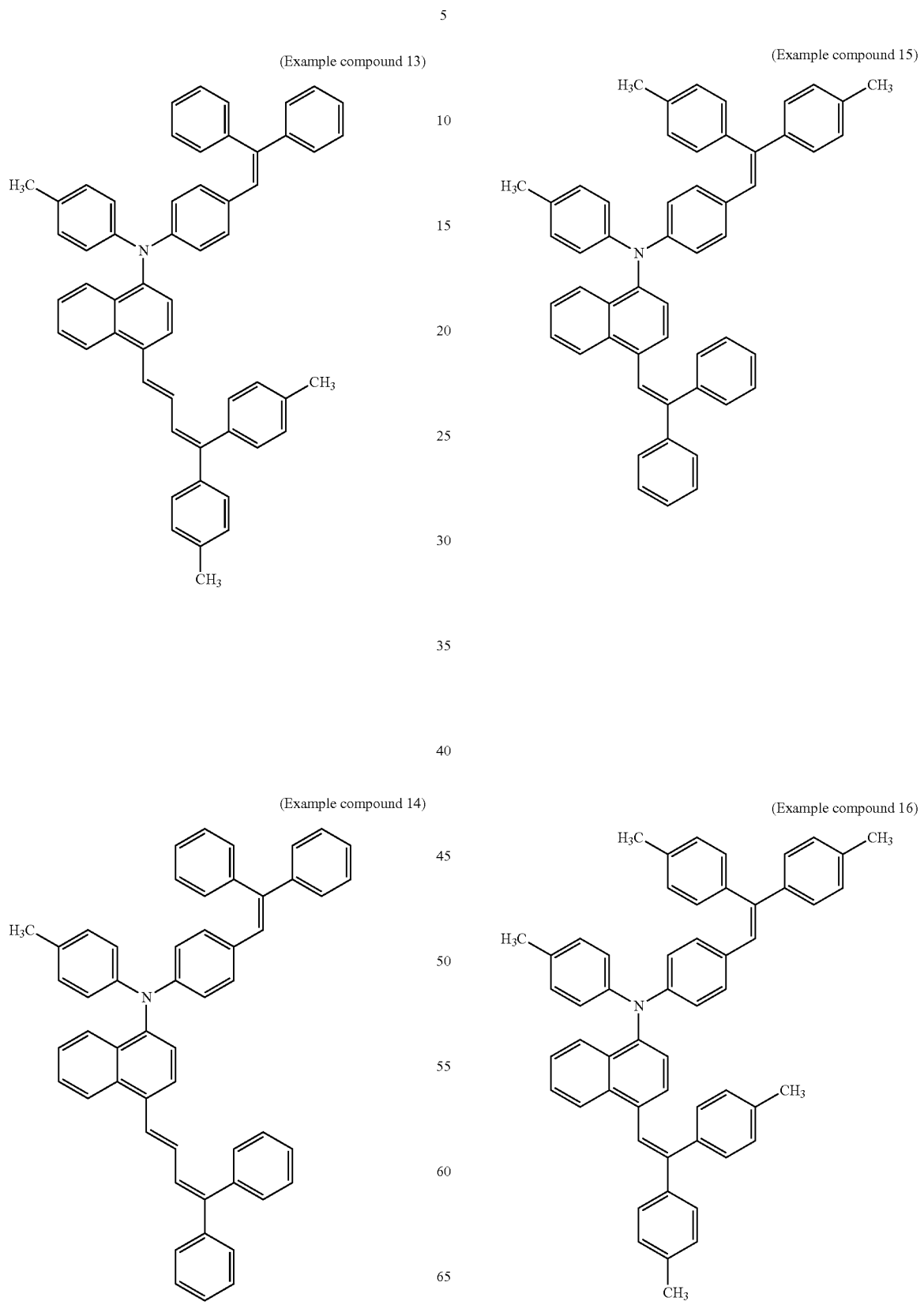

(Example compound 17)
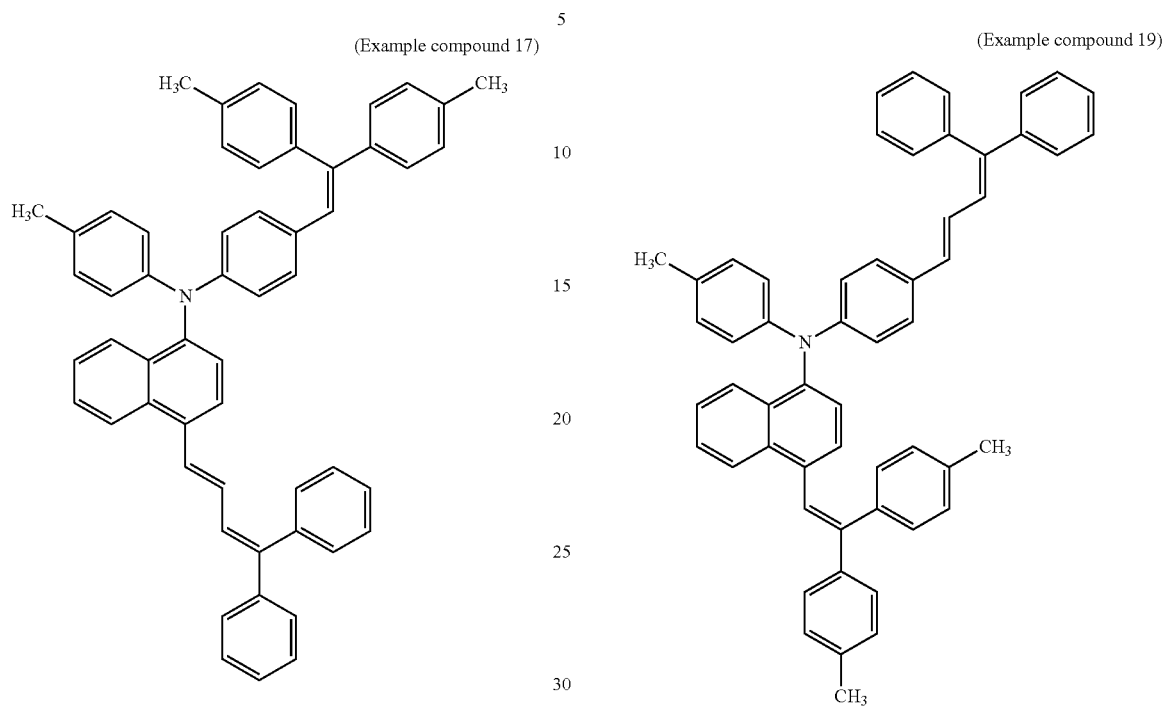
(Example compound 19)
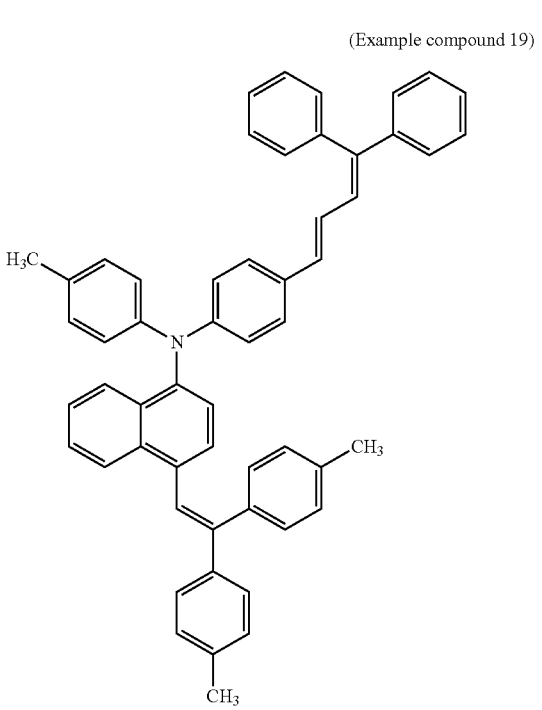
(Example compound 18)
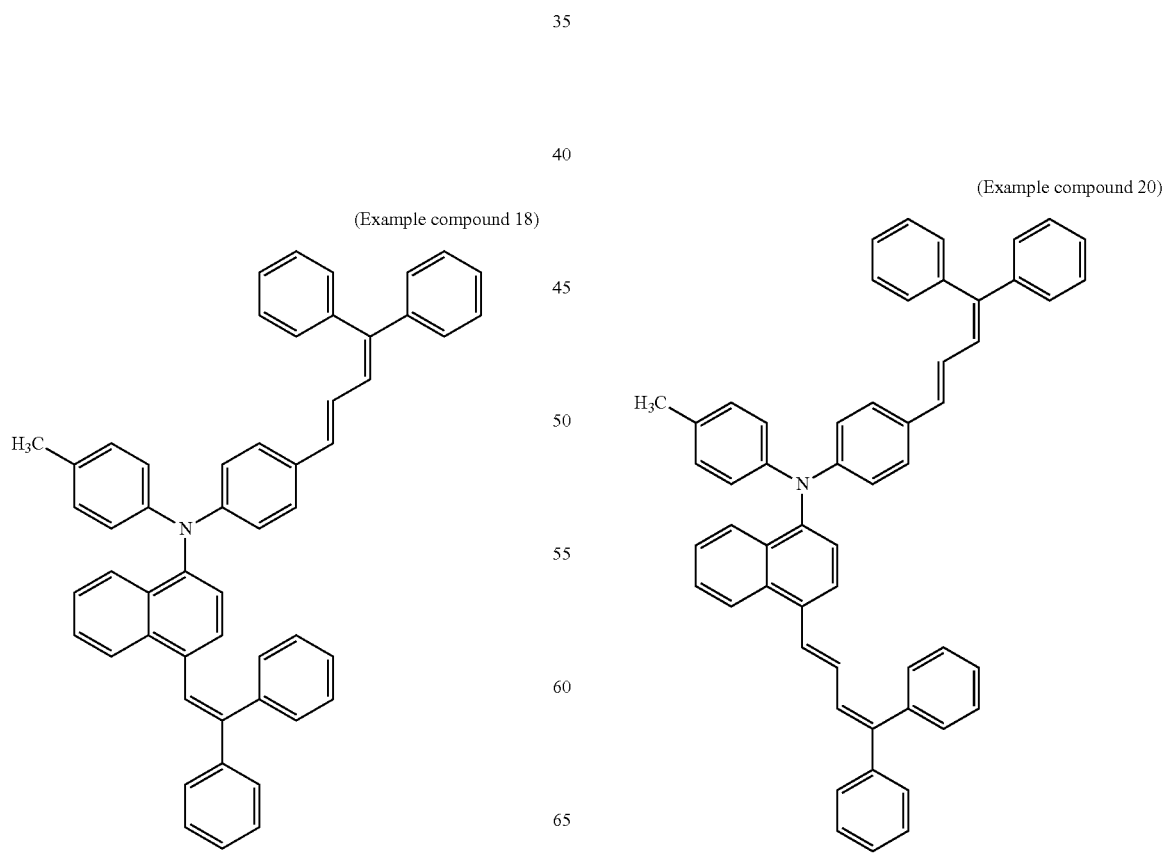
(Example compound 20)
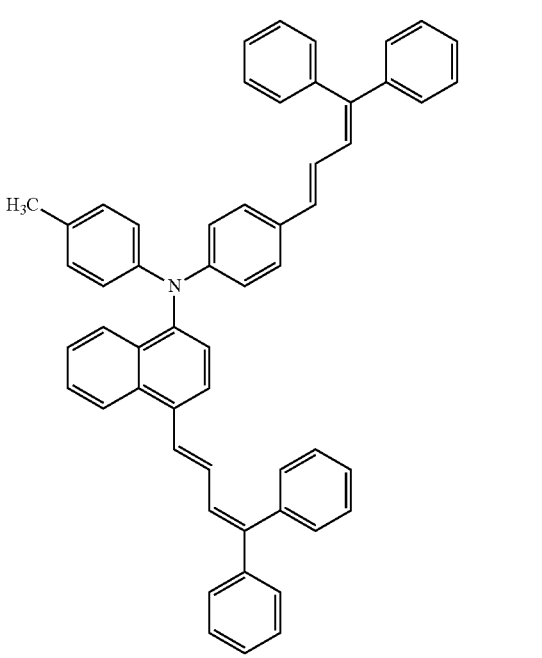

(Example compound 21)
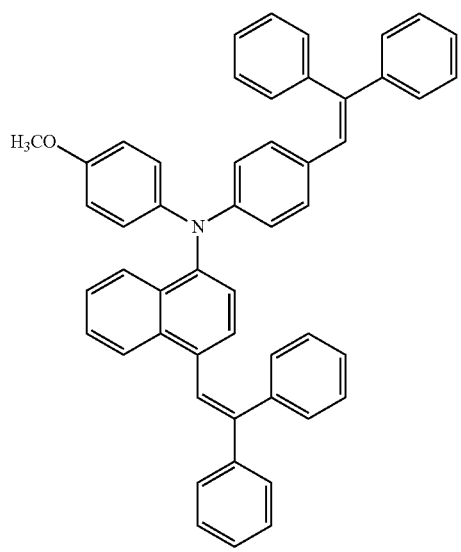
(Example compound 22)
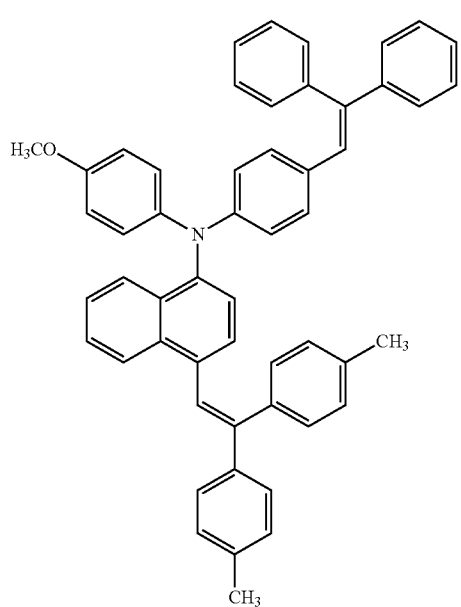
(Example compound 23)
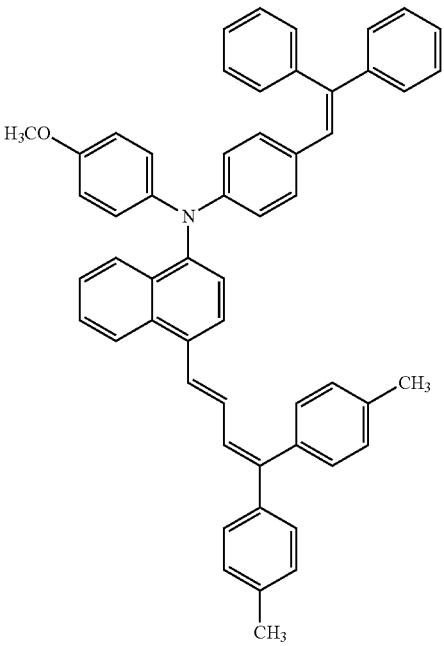
(Example compound 24)
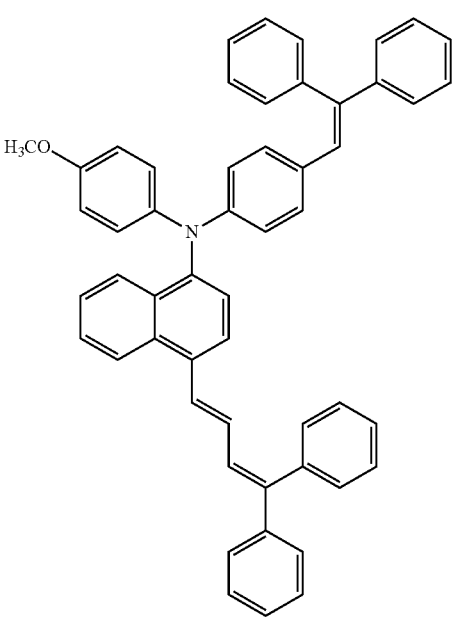

(Example compound 25)
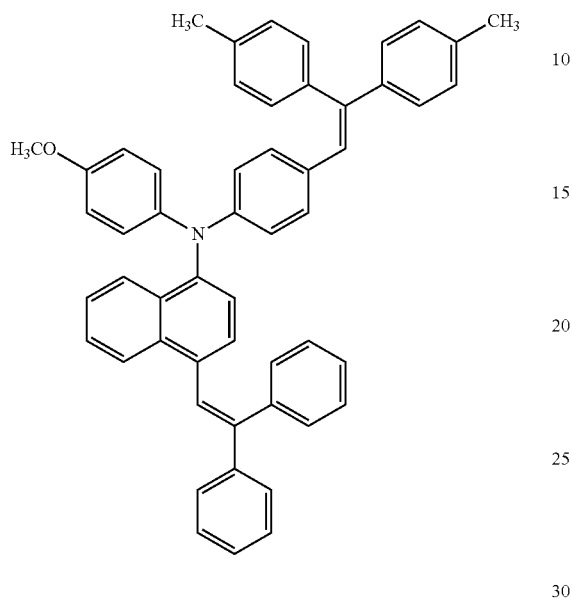
(Example compound 27)
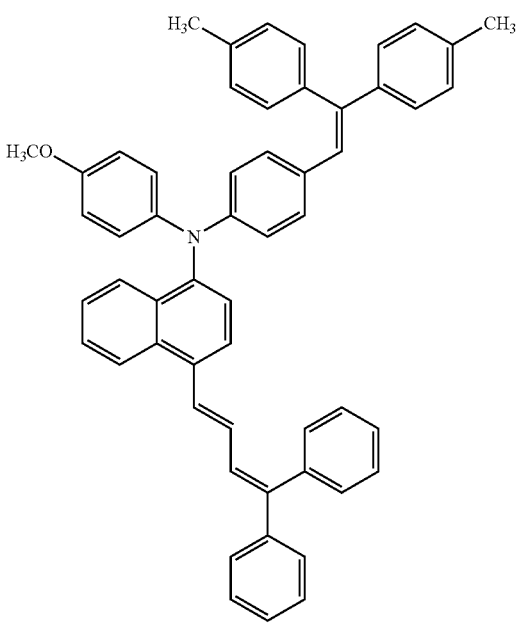
(Example compound 26)
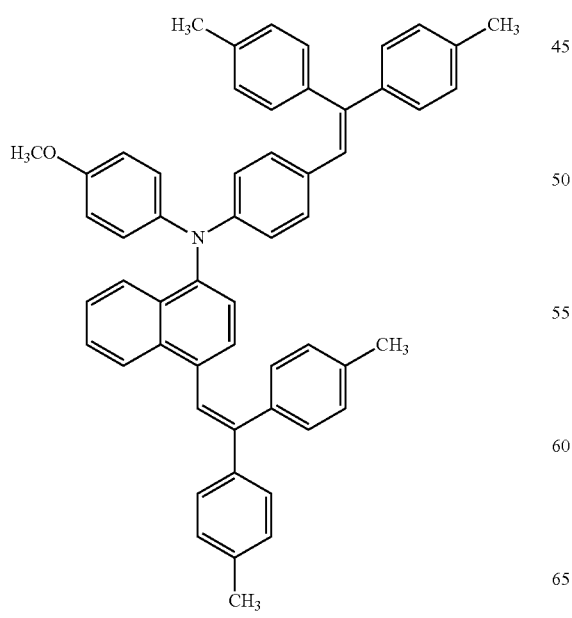
(Example compound 28)
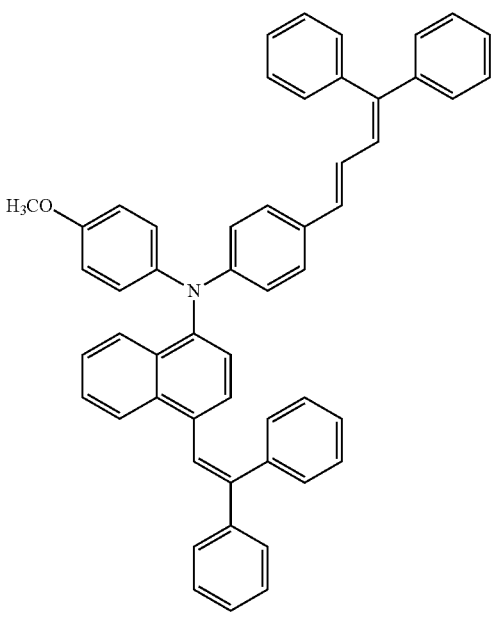

(Example compound 29)
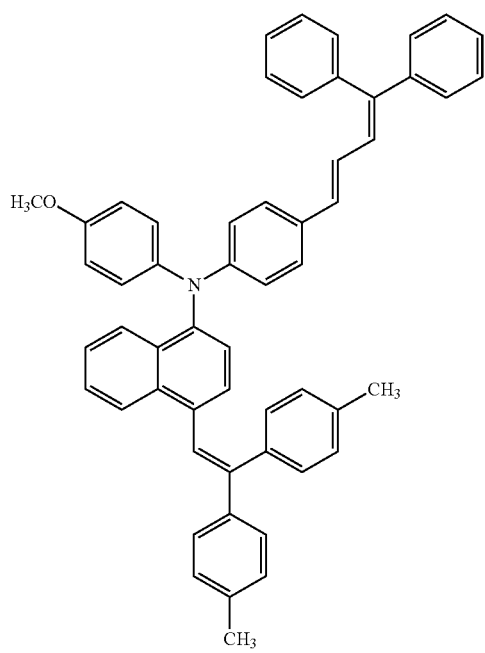
(Example compound 31)
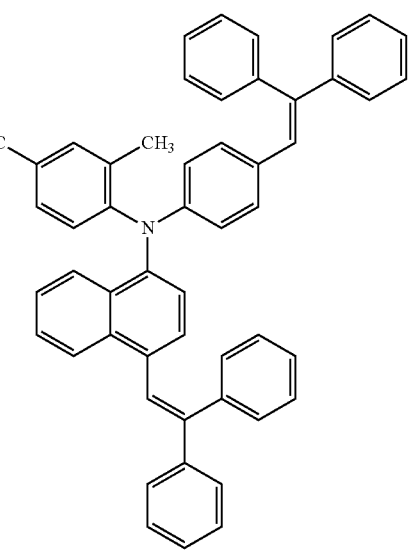
(Example compound 30)
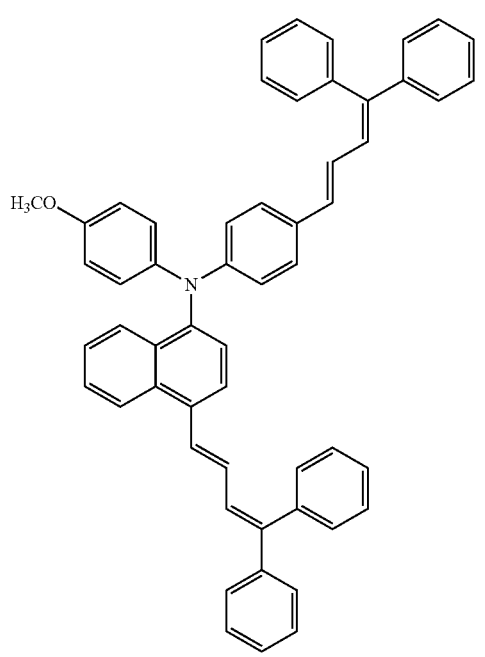
(Example compound 32)
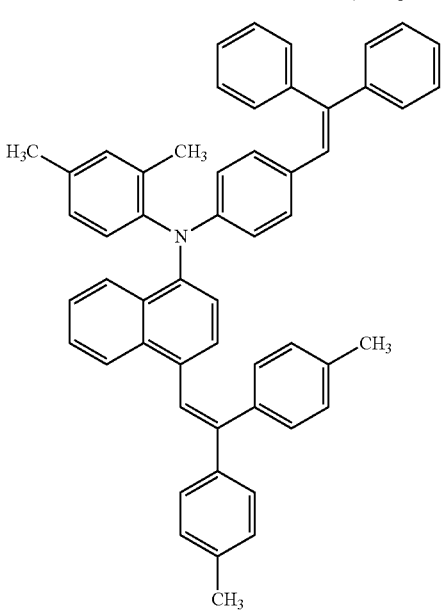

(Example compound 33)
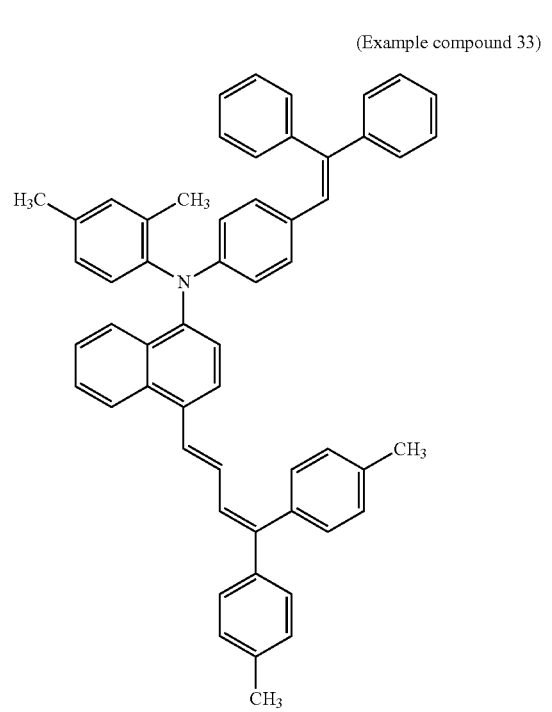
(Example compound 34)
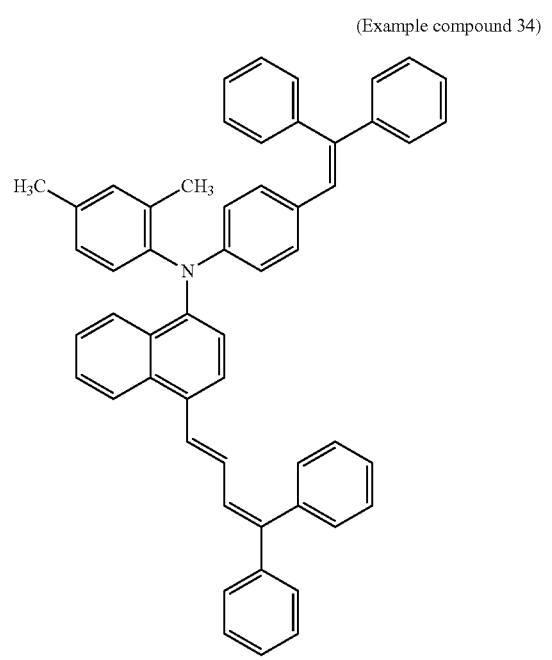
(Example compound 35)
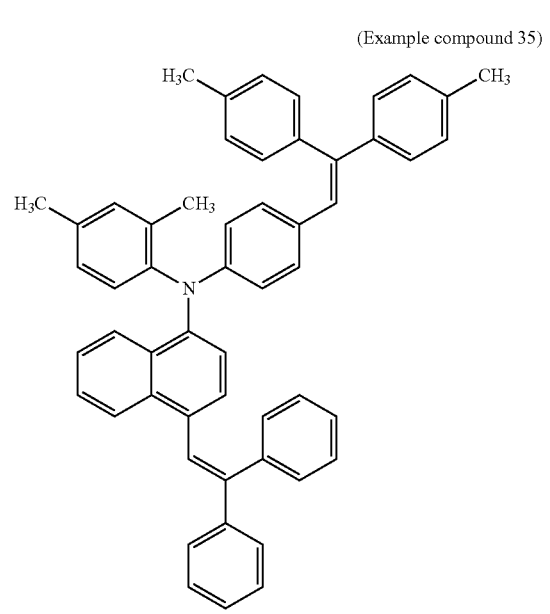
(Example compound 36)
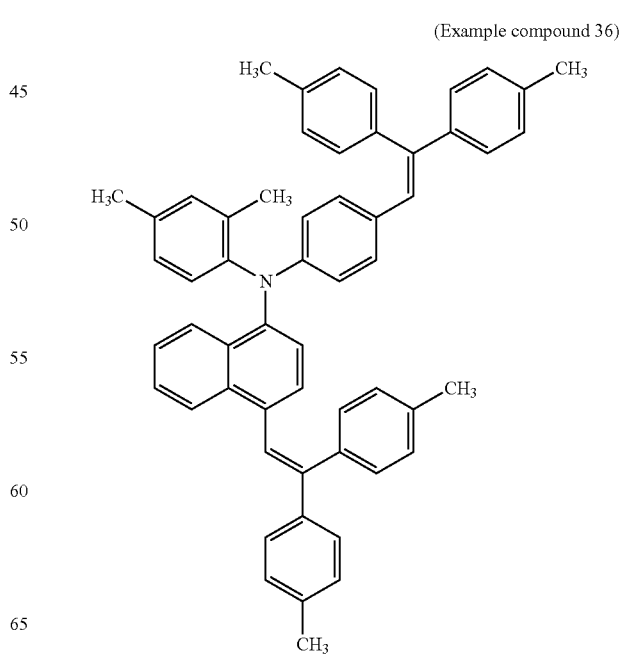

(Example compound 37)
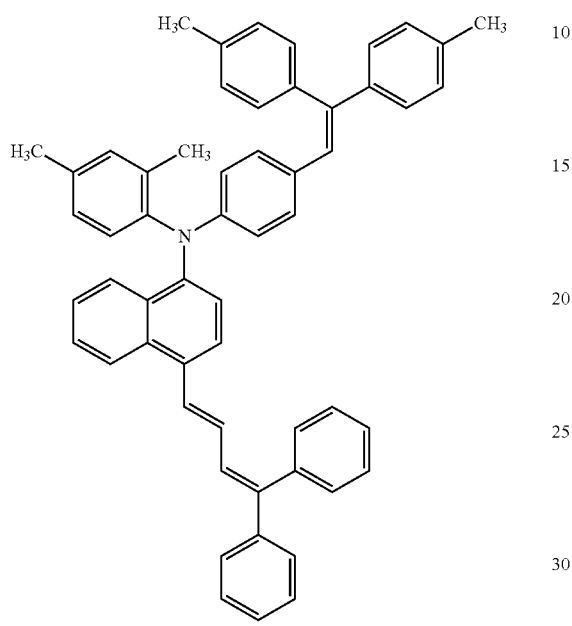
(Example compound 38)
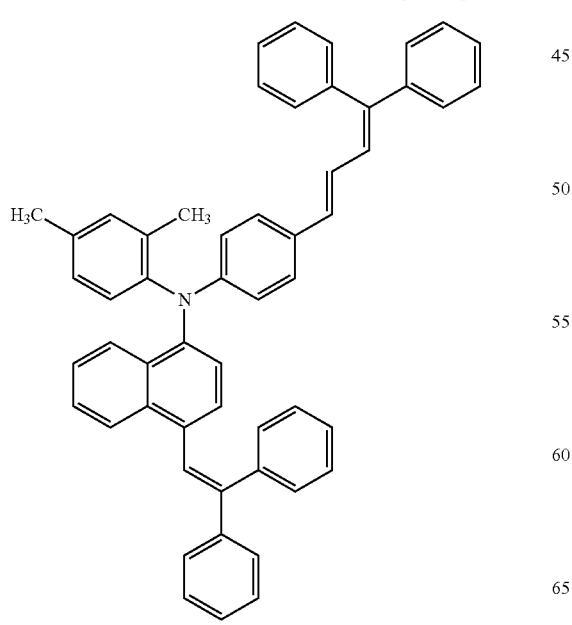
(Example compound 39)
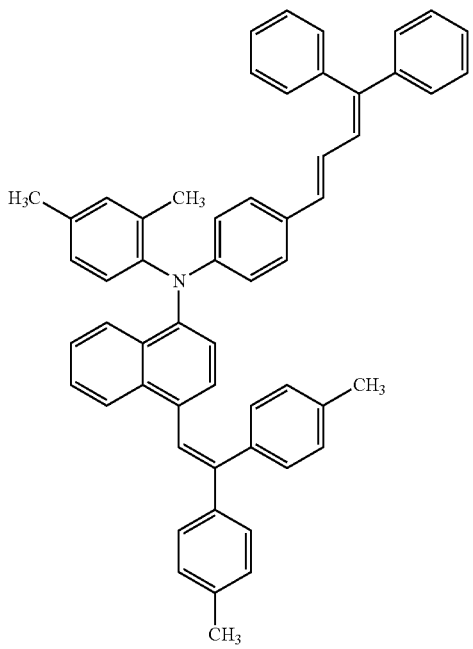
(Example compound 40)
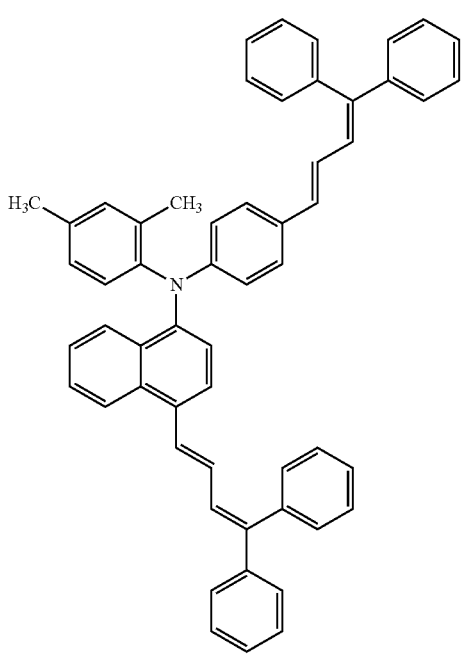

(Example compound 41)
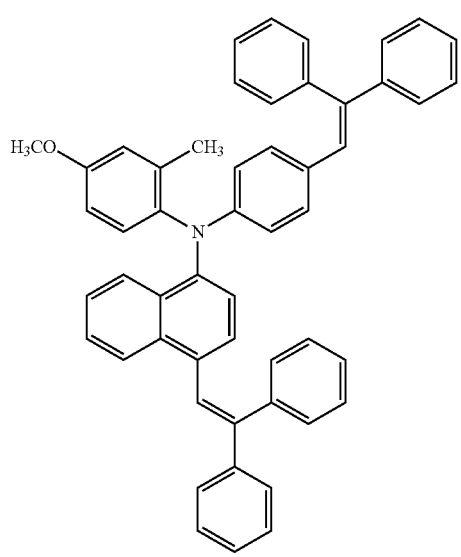
(Example compound 43)
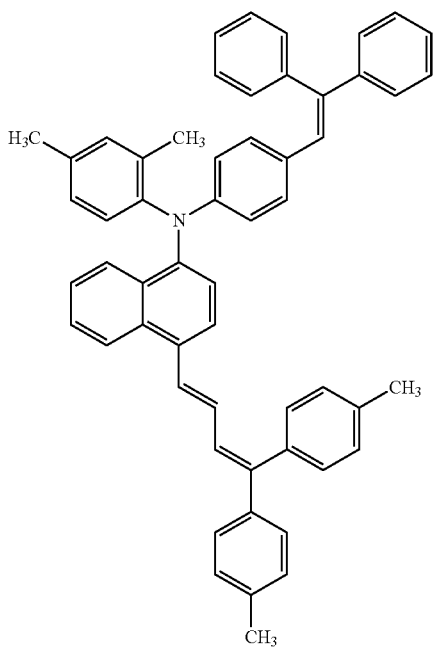
(Example compound 42)
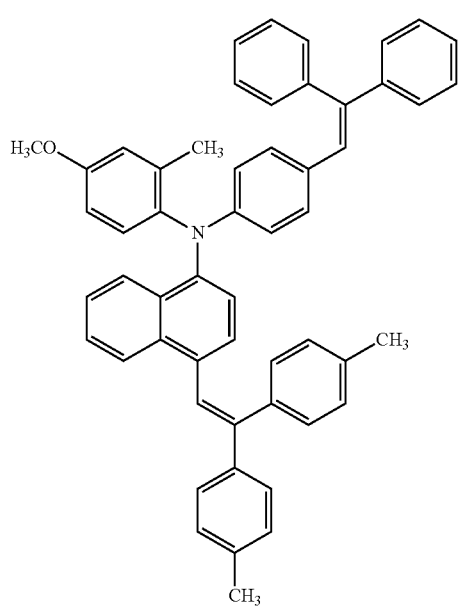
(Example compound 44)
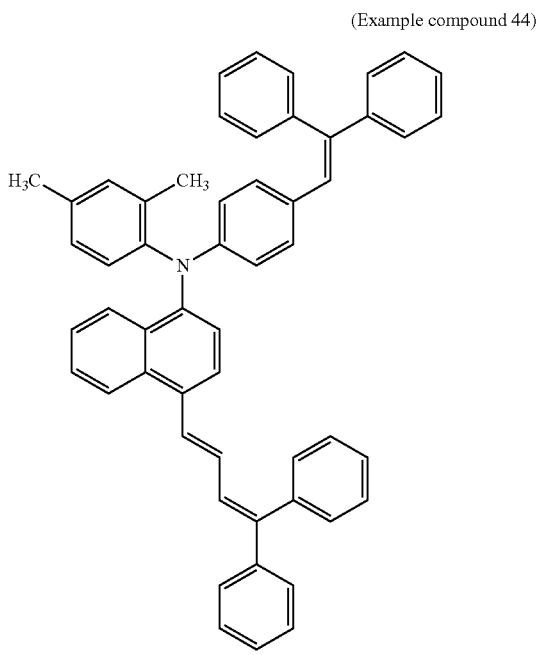

(Example compound 45)
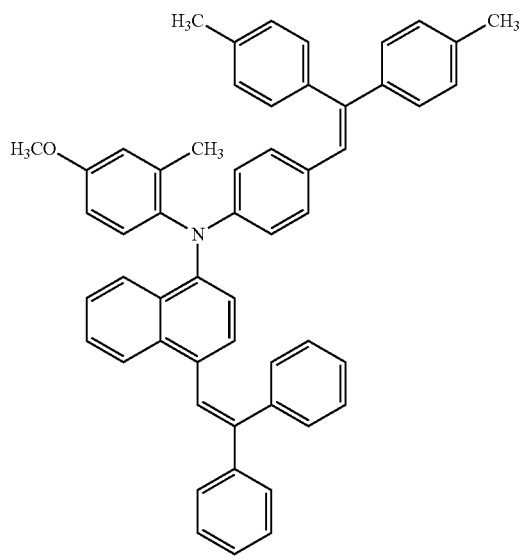
(Example compound 46)
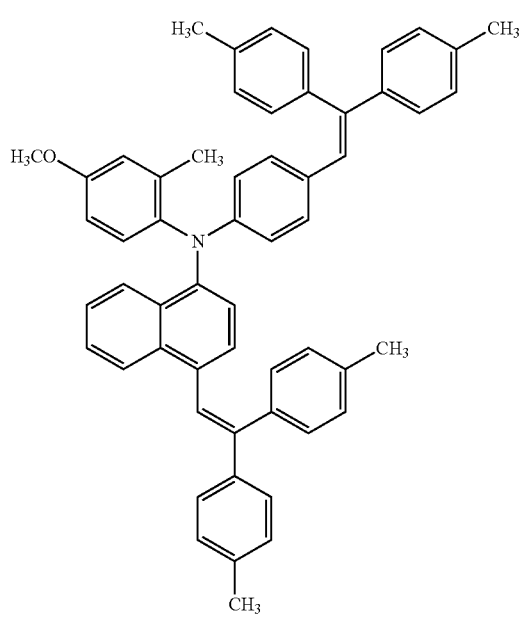
(Example compound 47)
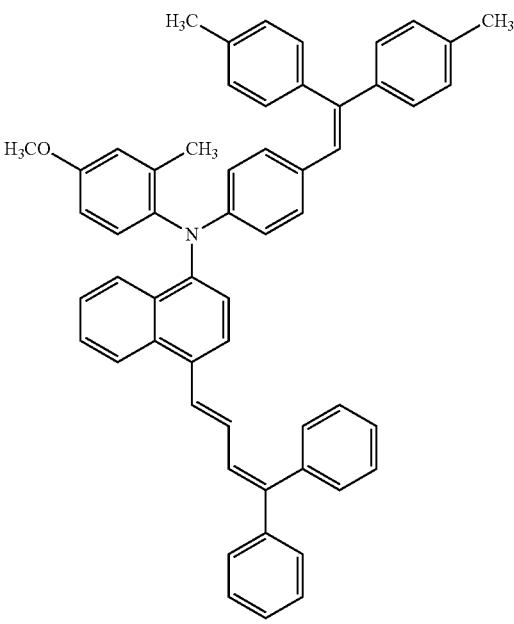
(Example compound 48)
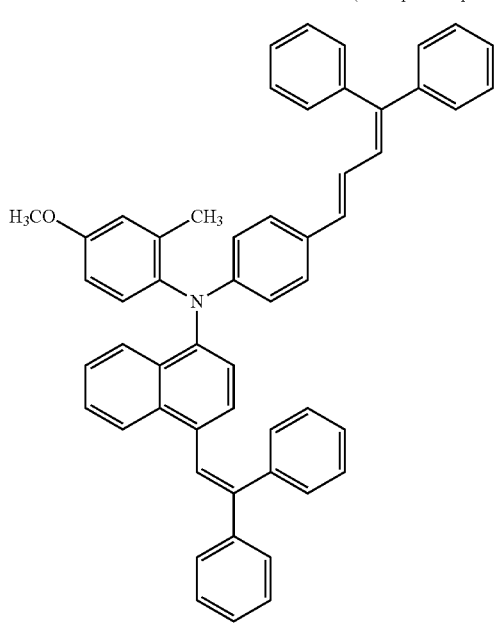

(Example compound 49)
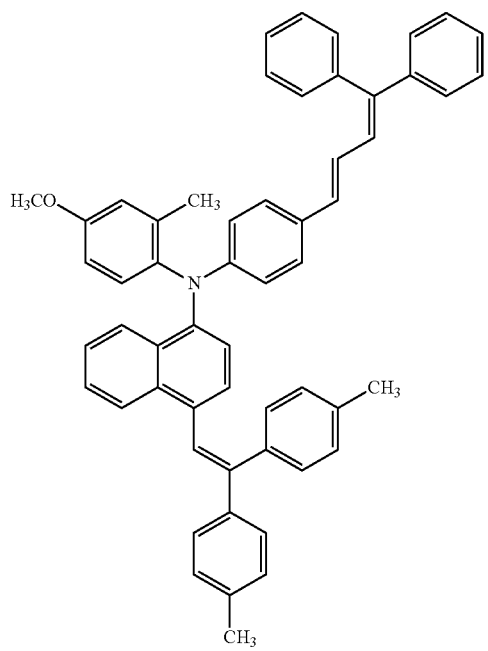
(Example compound 51)
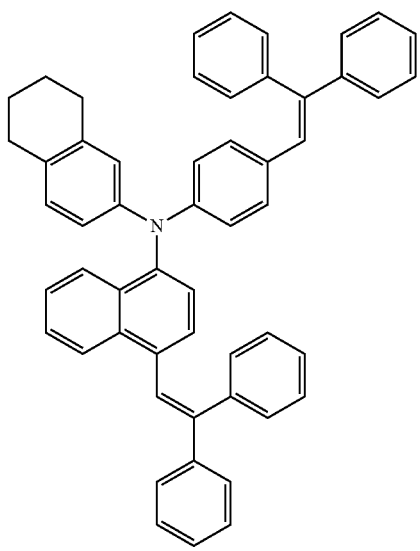
(Example compound 50)
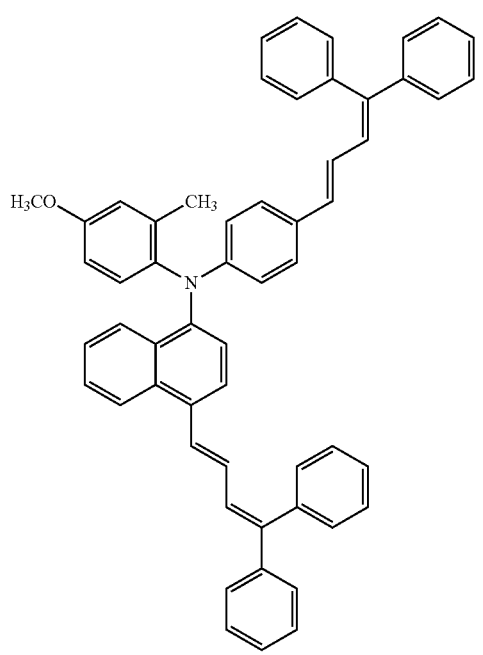
(Example compound 52)
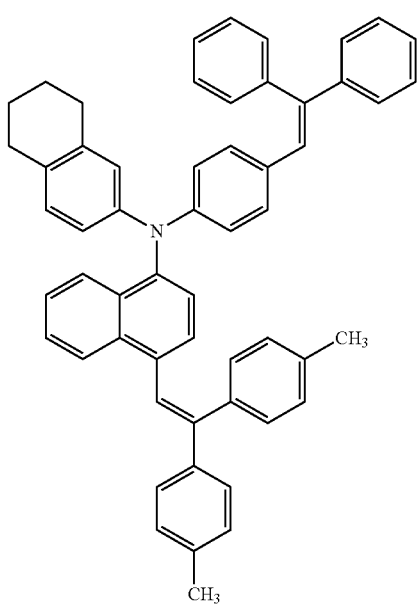

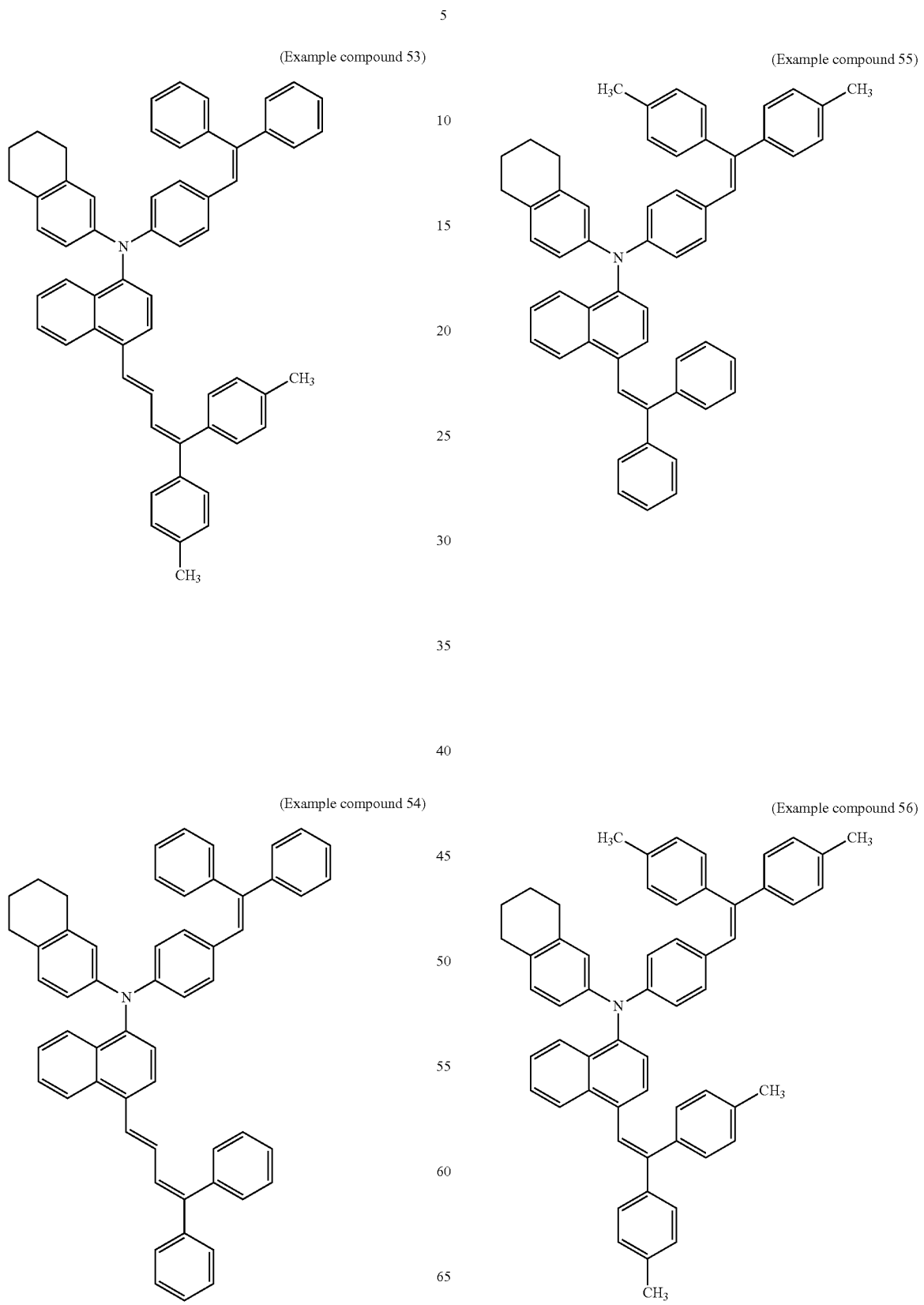

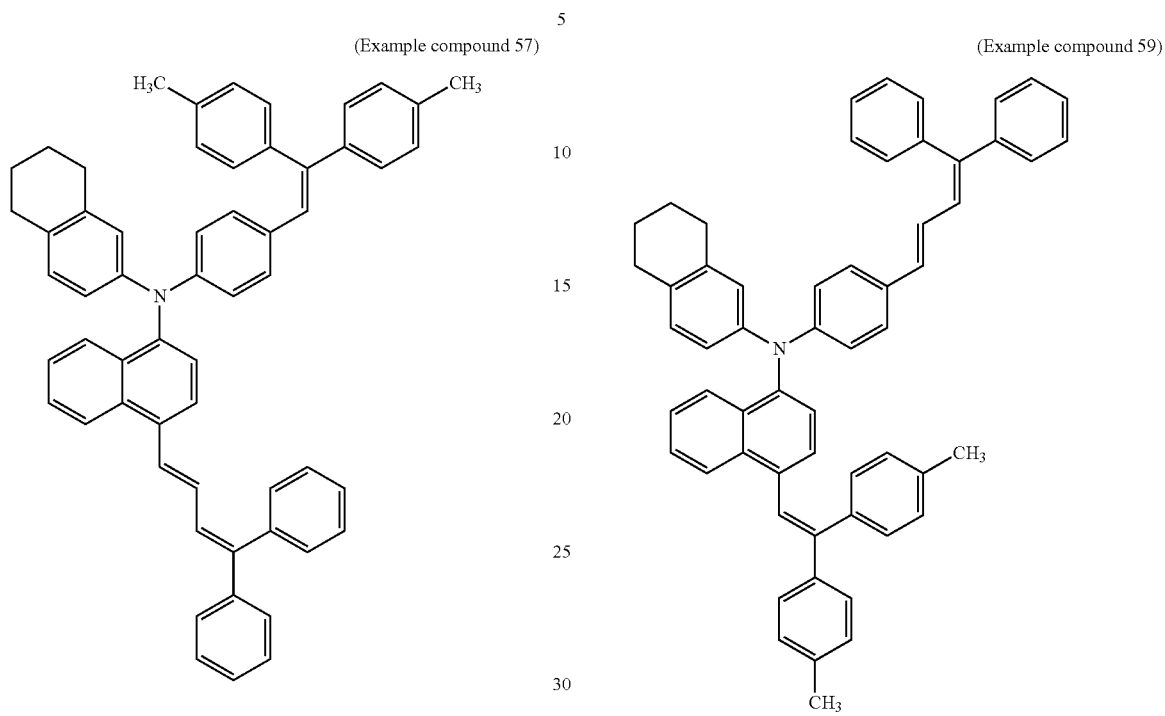
(Example compound 57)
(Example compound 59)
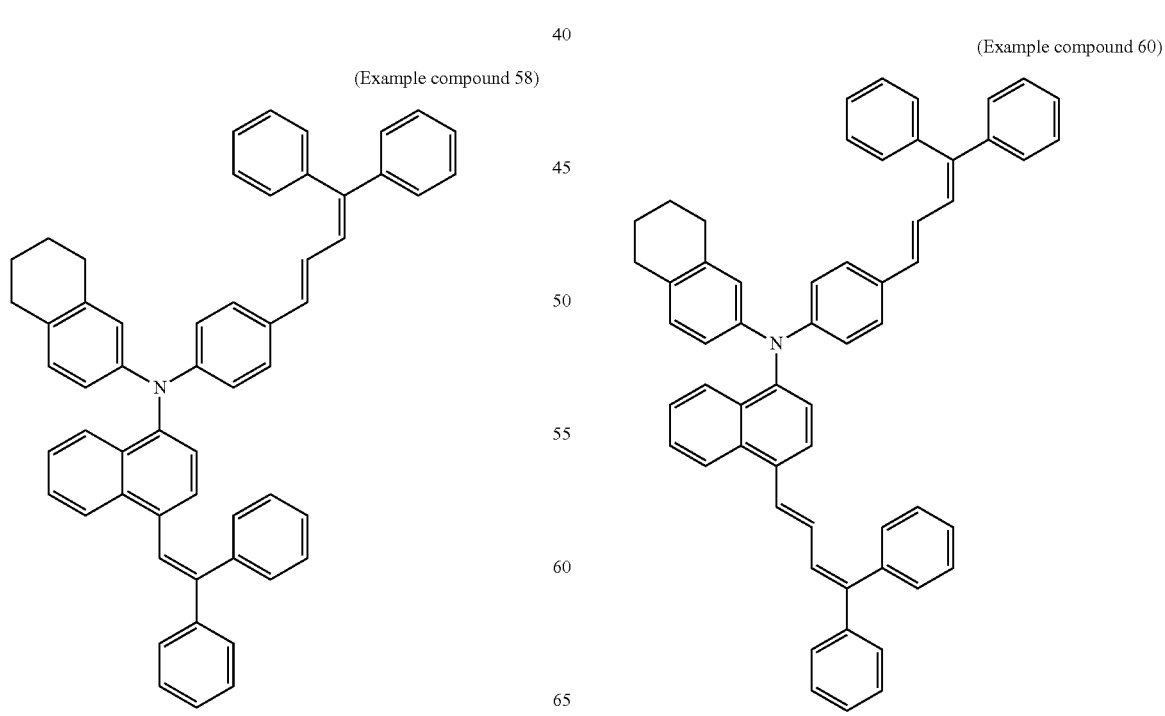
(Example compound 58)
(Example compound 60)

(Example compound 61)
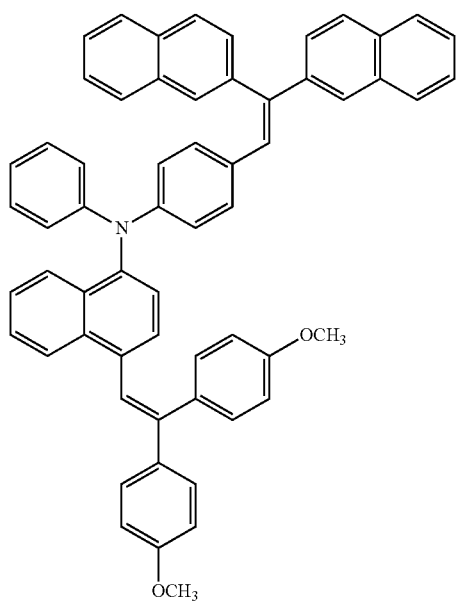
(Example compound 63)
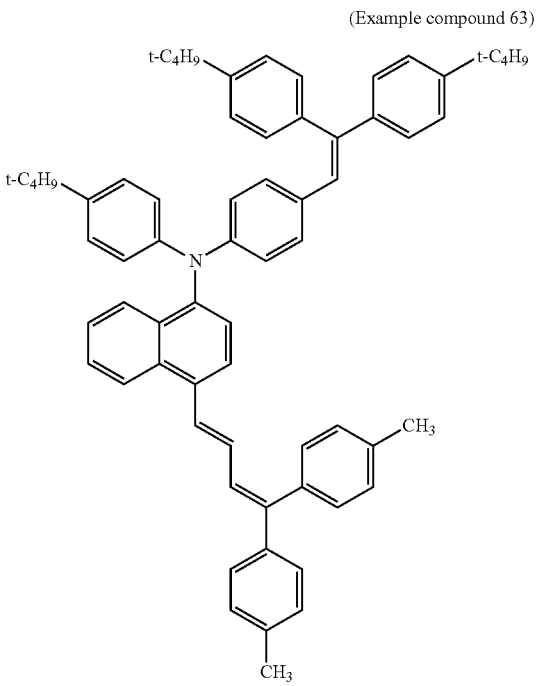
(Example compound 62)
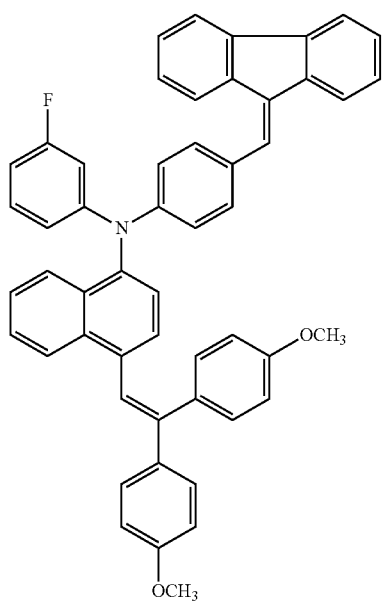
(Example compound 64)
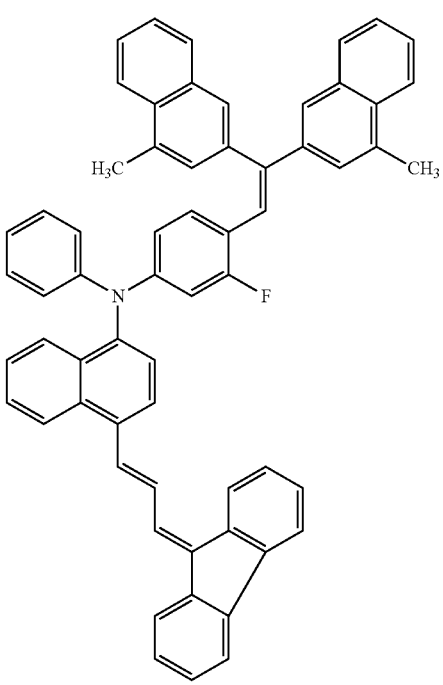

(Example compound 65)
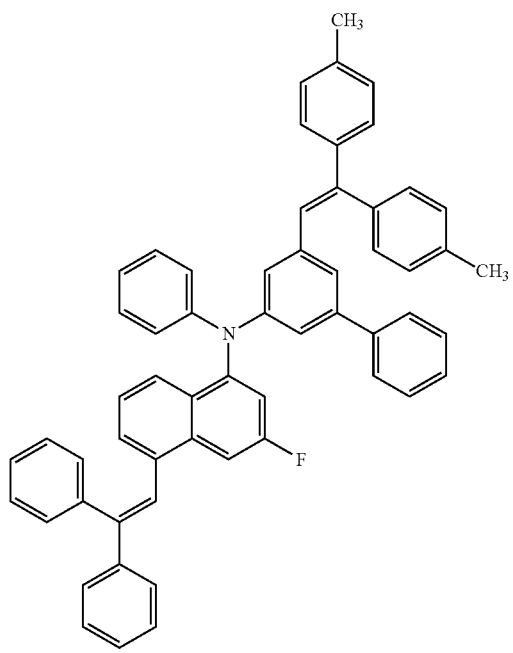
(Example compound 66)
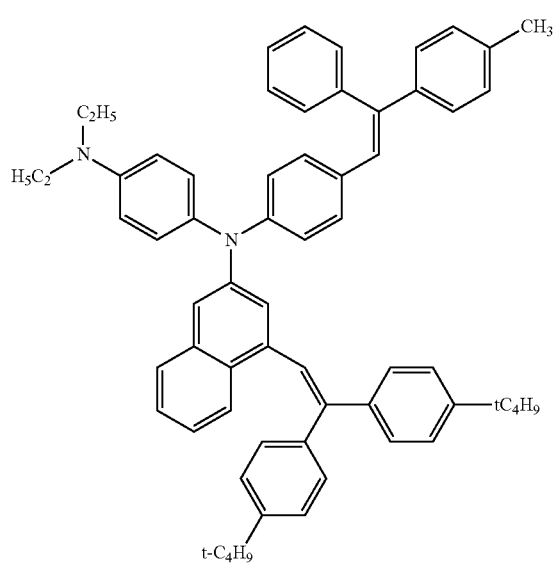
(Example compound 67)
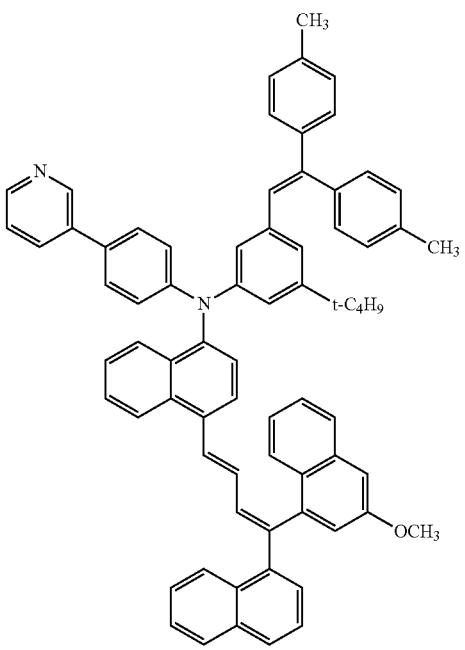
(Example compound 68)
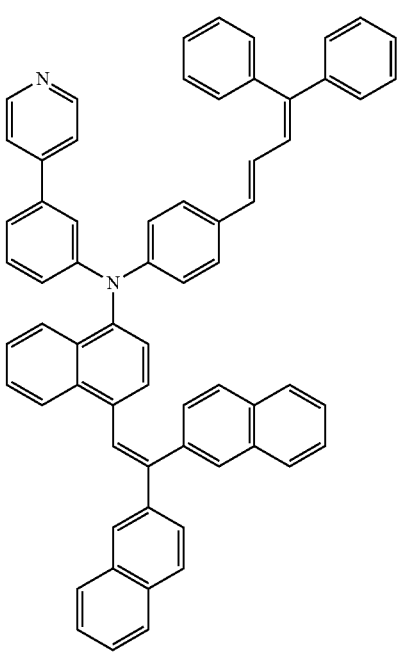

(Example compound 69)
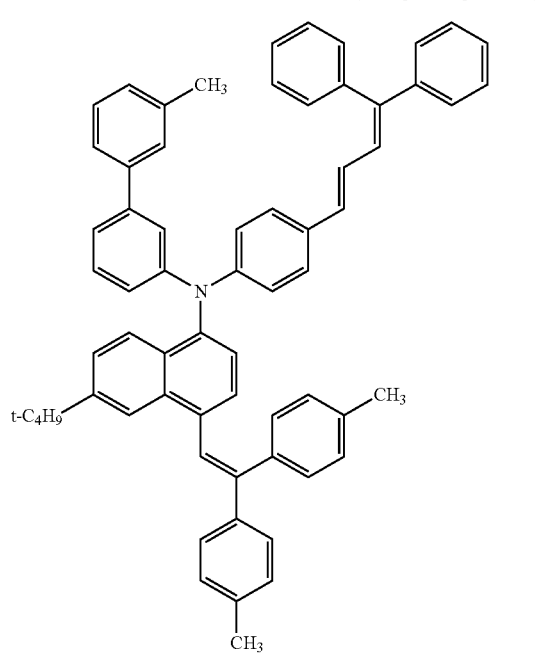
(Example compound 70)
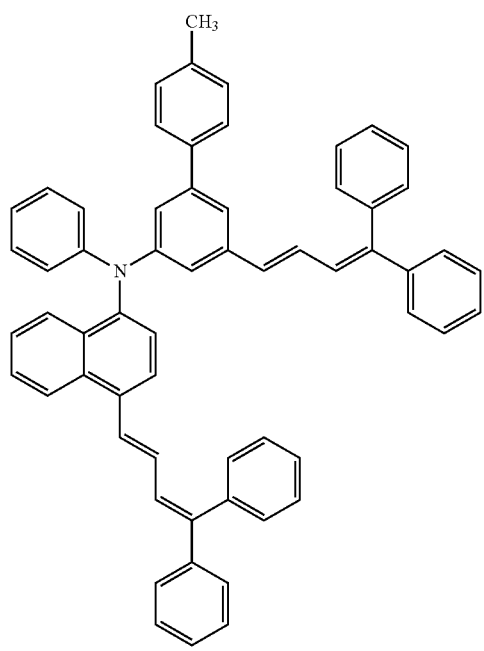
(Example compound 71)
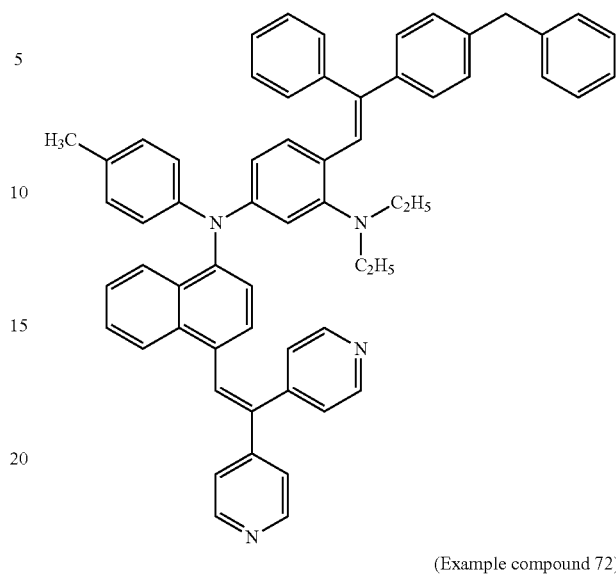
(Example compound 72)
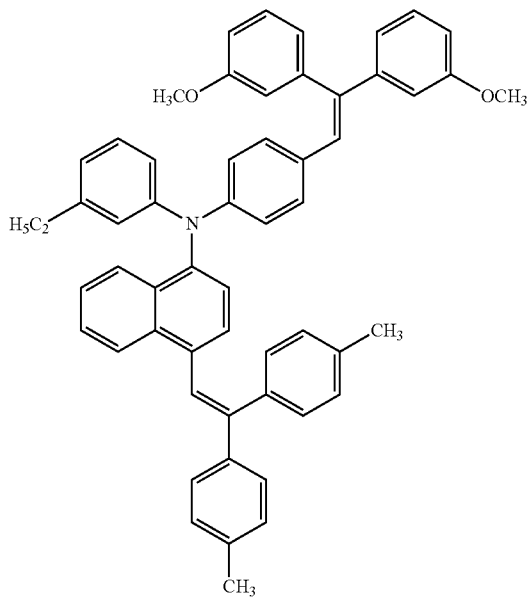
(Example compound 73)
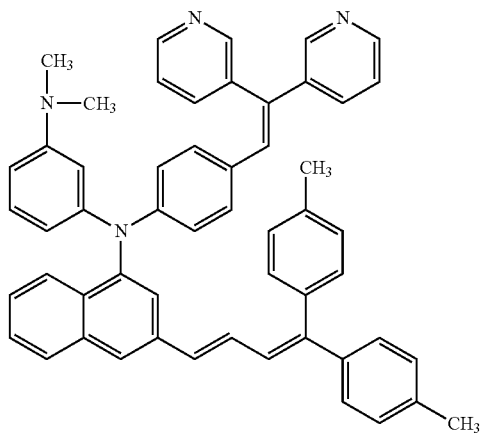

(Example compound 74)
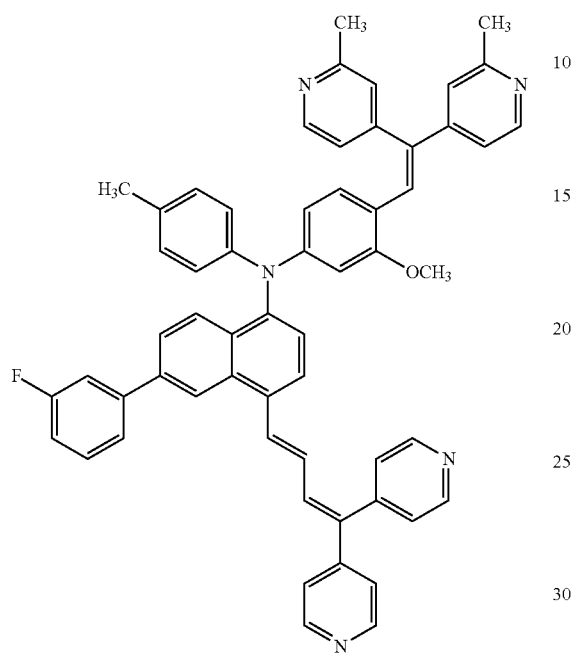
(Example compound 75)
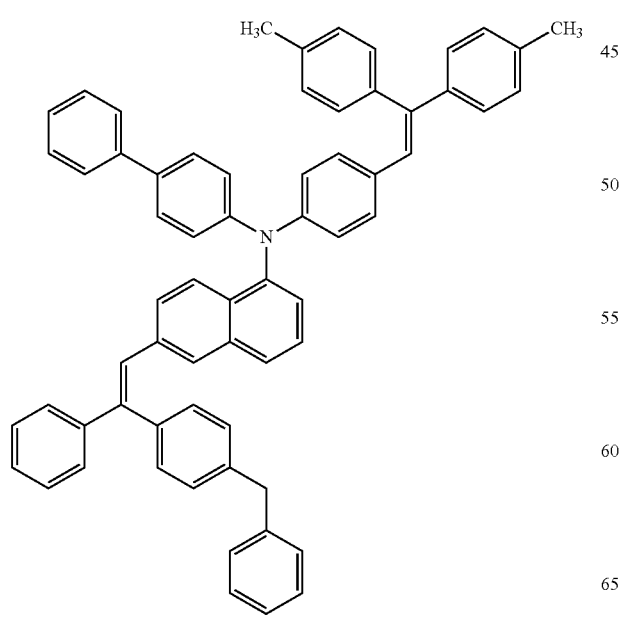
(Example compound 76)
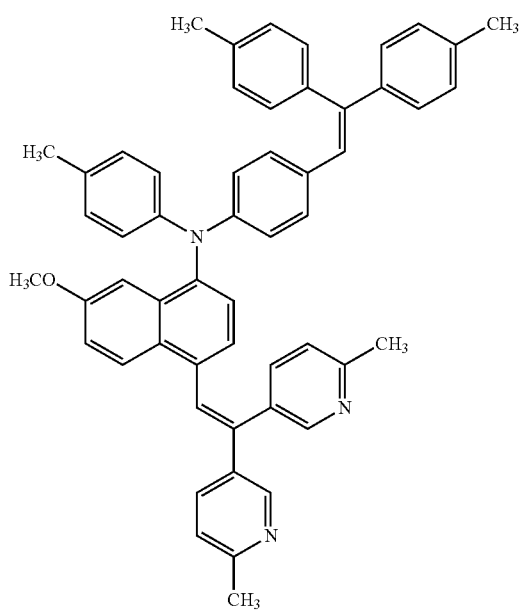
(Example compound 77)
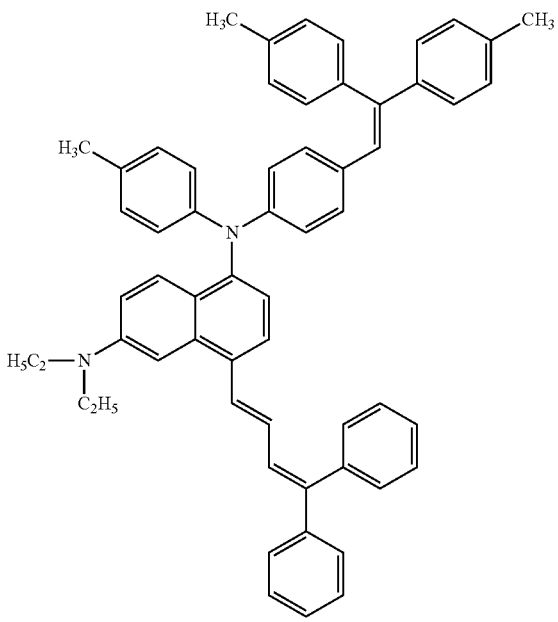

(Example compound 78)
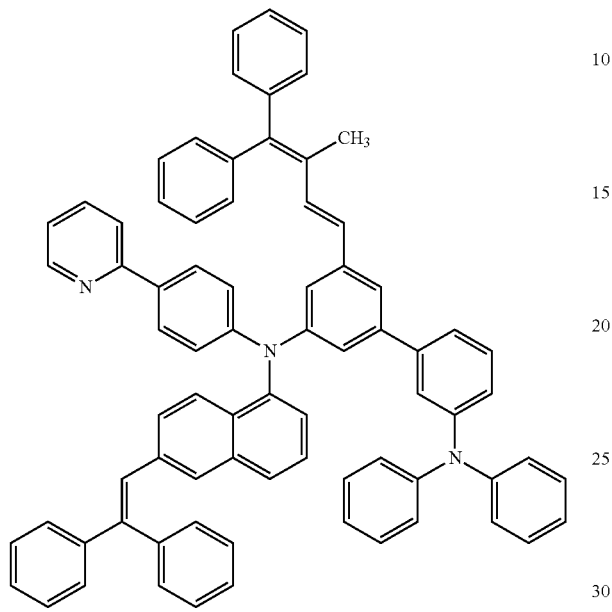
(Example compound 80)
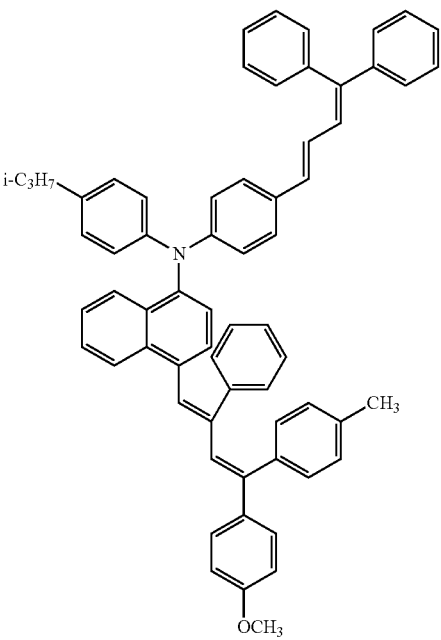
(Example compound 79)
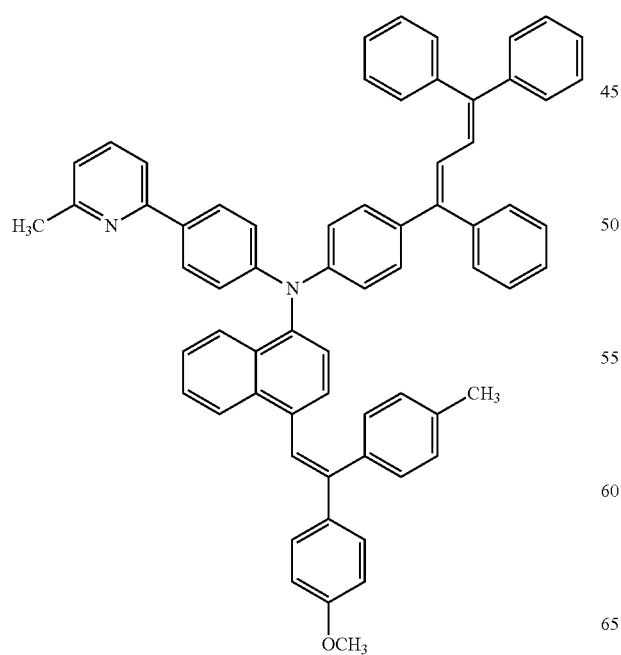
(Example compound 81)
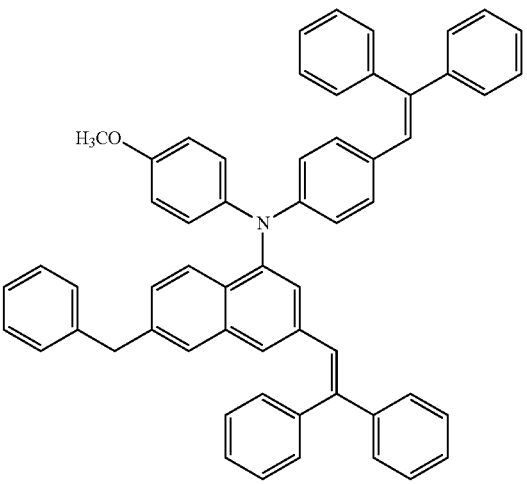

(Example compound 82)
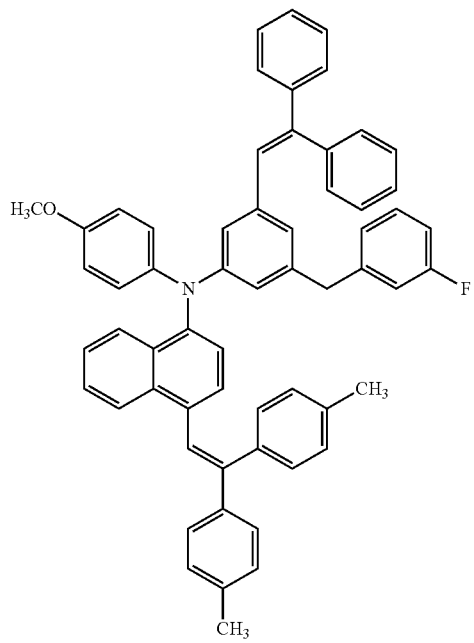
(Example compound 84)
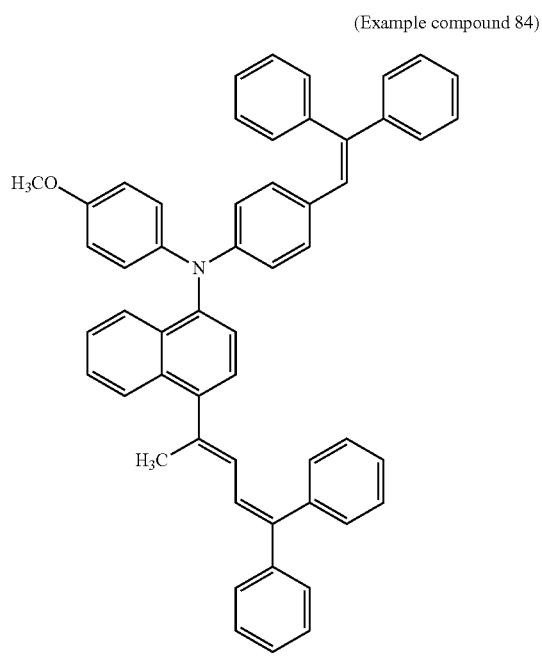
(Example compound 83)
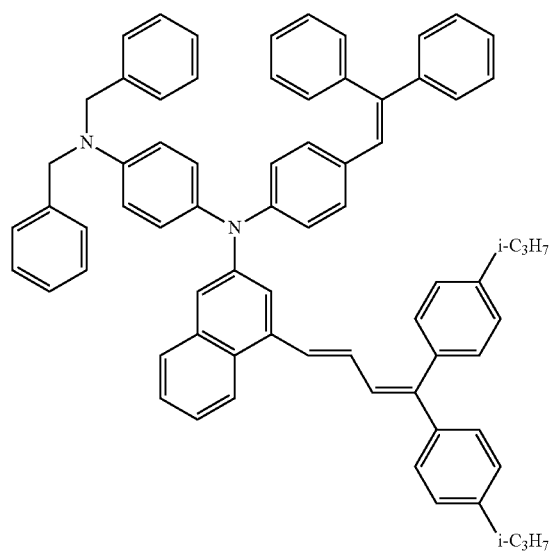
(Example compound 85)
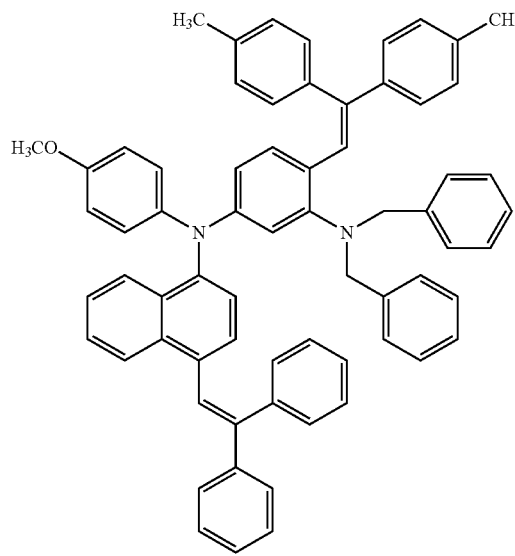

(Example compound 86)
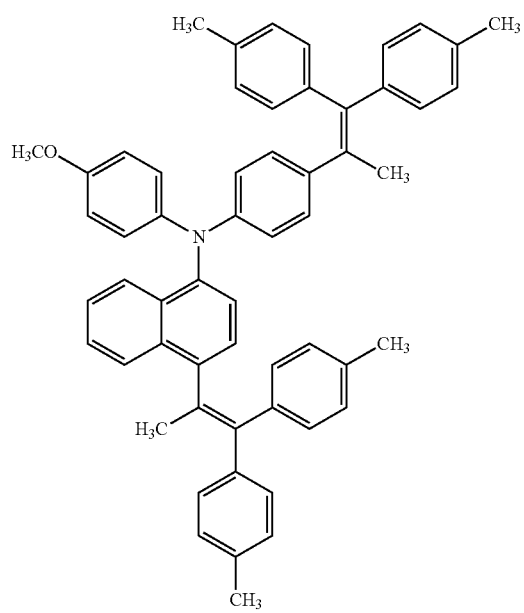
(Example compound 87)
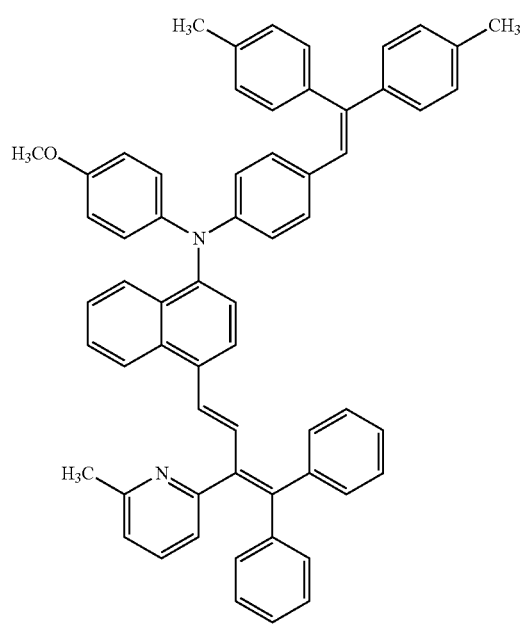
(Example compound 88)
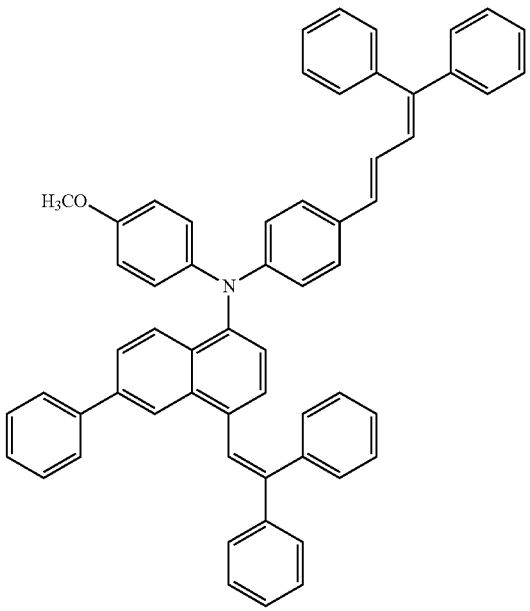
(Example compound 89)
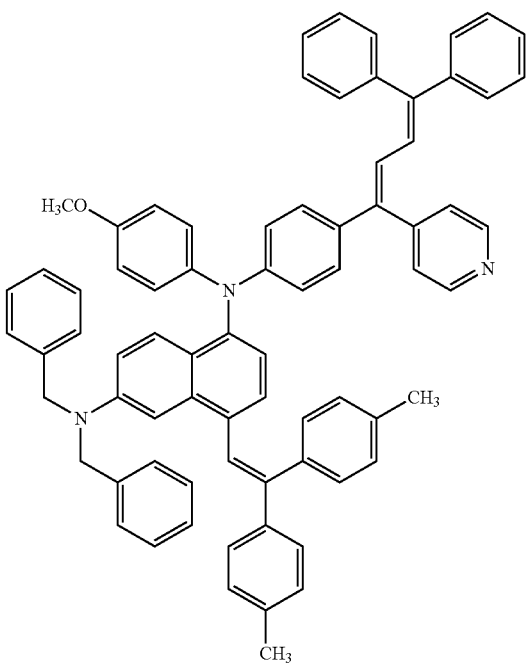

(Example compound 90)
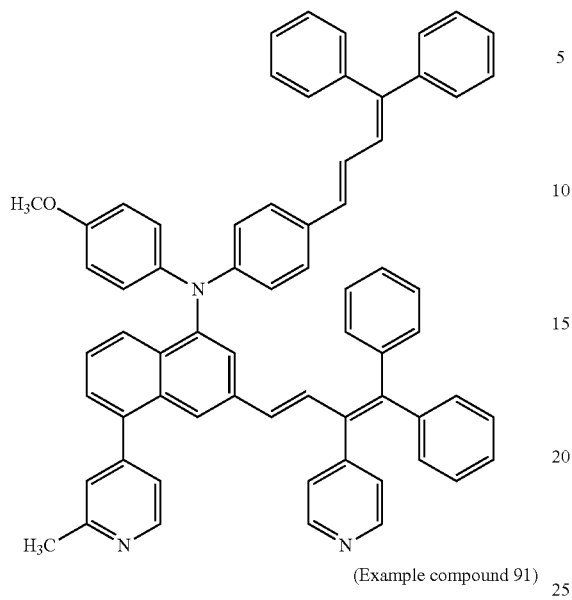
(Example compound 91)
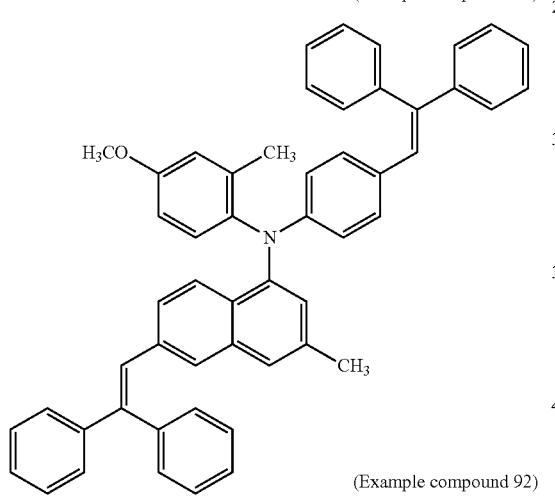
(Example compound 92)
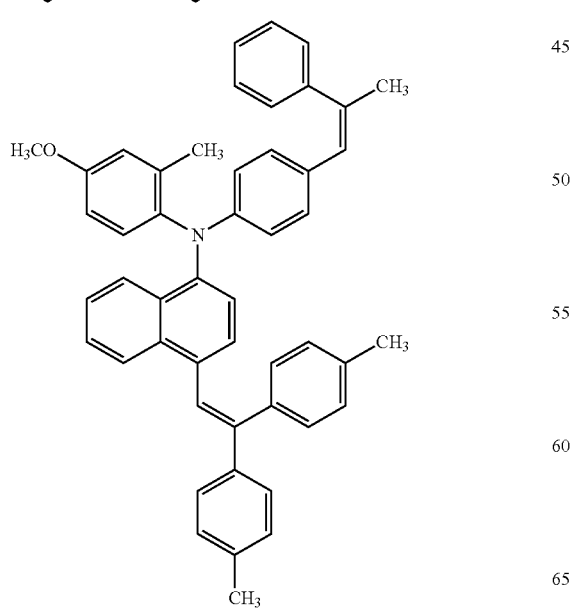
(Example compound 93)
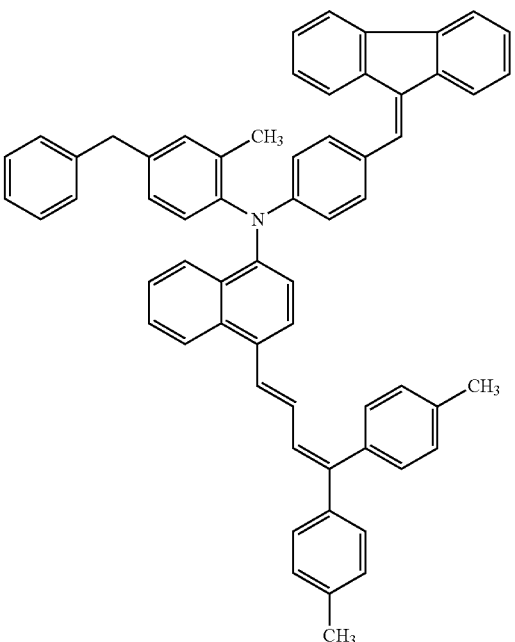
(Example compound 94)
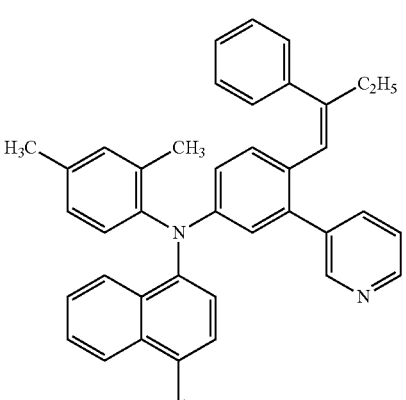
(Example compound 95)
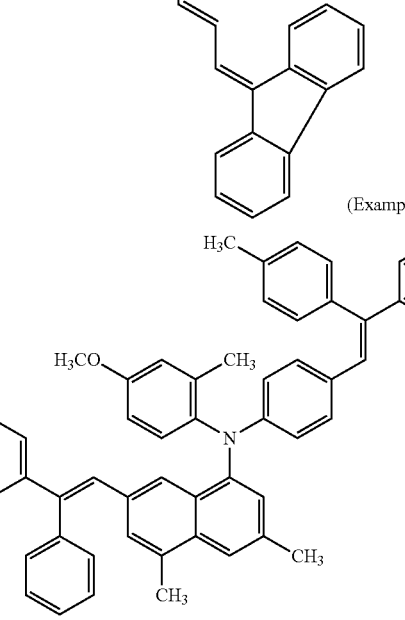

(Example compound 96)

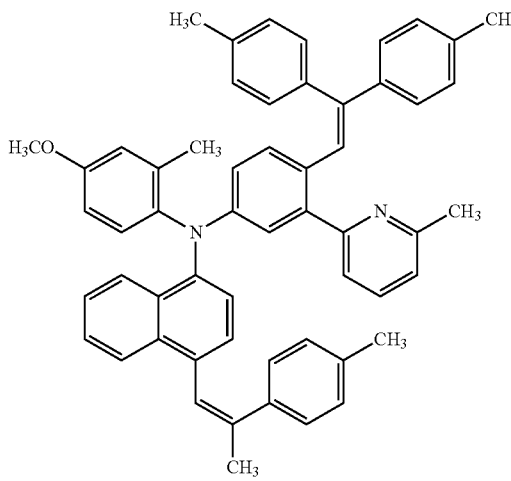

(Example compound 97)

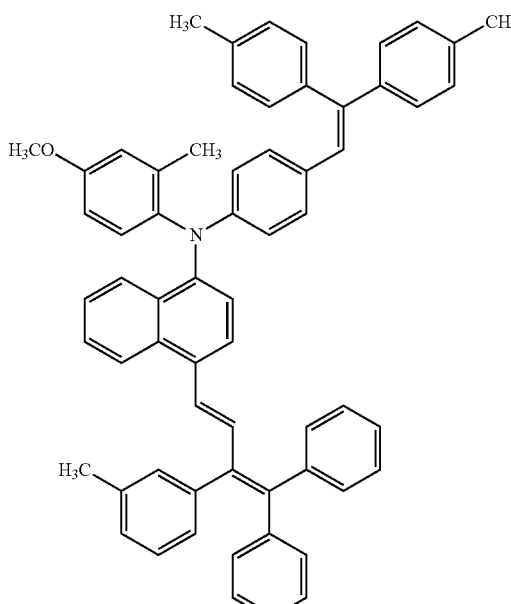

(Example compound 98)

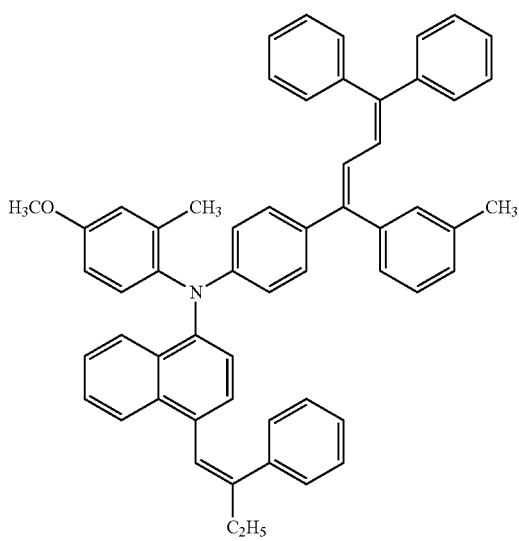

(Example compound 99)

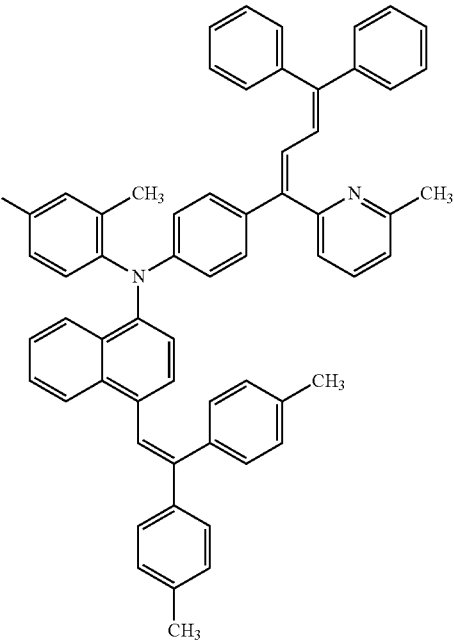

Among the diphenylnaphthylamine derivatives represented by the above general formula (1) of the invention, those having a structure represented by the following general formula (1') are preferred from the standpoint of properties as the charge-transporting agent.

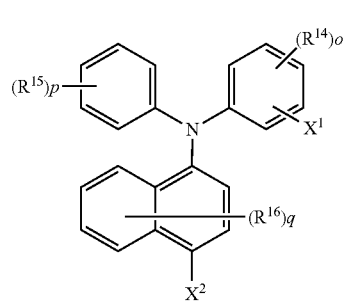

(1')

In the formula, o is a number corresponding to j in the above general formula (1) and is an integer of 0 to 4, p is a number corresponding to k in the above general formula (1) and is an integer of 0 to 5, q is a number corresponding to l in the above general formula (1) and is an integer of 0 to 6.

$R^{14}$, $R^{15}$ and $R^{16}$ are, respectively, groups corresponding to $R^1$, $R^2$ and $R^3$ in the above general formula (1), $X^1$ is a monovalent group represented by the above general formula (1a), and $X^2$ is a monovalent group represented by the above general formula (1b).

Namely, the diphenylnaphthylamine derivative represented by the above general formula (1') has the diarylamino group and the group $X^2$ bonded to the naphthalene ring at specific positions. Among the above-mentioned many Example compounds, those Example compounds 1 to 64, 67 to 72, 74, 76, 77, 79, 80, 82, 84 to 89, 92 to 94, and 96 to 99 are the diphenylnaphthylamine derivatives represented by the general formula (1').

In the invention, further, among the diphenylnaphthylamine derivatives represented by the above general formula (1'), those represented by the following general formula (1") or (1'") are more preferred.

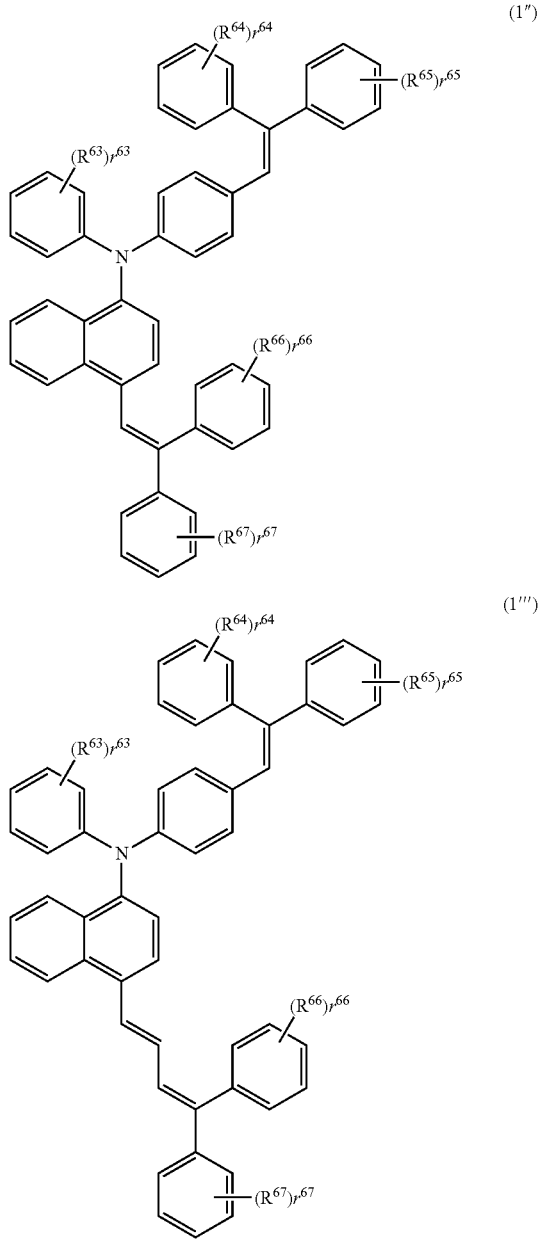

In the above general formula (1") or (1'"), $r^{63}$ to $r^{67}$ may be the same or different, and are integers of 0 to 5.

$R^{63}$ to $R^{67}$ may be the same or different, and are groups selected from the group consisting of alkyl group having 1 to 6 carbon atoms; alkoxy group having 1 to 6 carbon atoms; halogen atom; aromatic hydrocarbon group; condensed polycyclic aromatic group; aromatic heterocyclic group; and disubstituted amino group having, as substituents, alkyl groups having 1 to 6 carbon atoms, alkenyl groups having 2 to 6 carbon atoms, aralkyl groups, aromatic hydrocarbon groups or aromatic heterocyclic groups.

The groups $R^{63}$ to $R^{67}$ are the same as the groups $R^1$ to $R^3$ in the above general formula (1), and their concrete examples may be those exemplified as $R^1$ to $R^3$.

Further, when $R^{63}$, $R^{64}$, $R^{65}$, $R^{66}$ are present in plural numbers, the plurality of $R^{63}$, $R^{64}$, $R^{65}$, $R^{66}$ and $R^{67}$ may be each the same or different, and may be bonded together to form a ring structure.

Among the diphenylnaphthylamine derivatives represented by the general formula (1), the diphenylnaphthylamine derivative represented by the above general formula (1") or (1'") exhibits particularly excellent charging-transporting property, and can be most desirably used as a charge-transporting agent for the production of an organic photosensitive material for electrophotography.

<Preparation of diphenylnaphthylamine Derivatives>

The above diphenylnaphthylamine derivatives of the present invention can be synthesized by using a diphenylnaphthylamine compound represented by the following general formula (2) as a starting material.

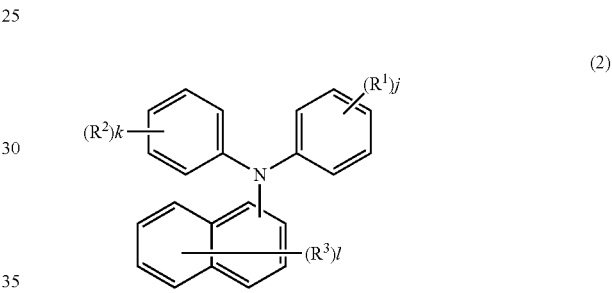

wherein $R^1$ to $R^3$, j, k and l are the same as those defined in the general formula (1).

The above diphenylnaphthylamine compound is a known compound and has been disclosed, for example, in JP-B-4-066023 (patent document 14). The diphenylnaphthylamine derivative of the invention represented by the above general formula (1) is prepared by introducing the group $X^1$ into the diphenylnaphthylamine compound and, next, introducing the group $X^2$ therein.

(Introduction of the Group $X^1$)

To introduce the group $X^1$ into the diphenylnaphthylamine compound of the general formula (2), first, a carbonyl group (formyl group or ketone group) is introduced into the benzene ring bonded to the nitrogen atom of the above compound to synthesize a carbonyl compound represented by the following general formula (3) or (3').

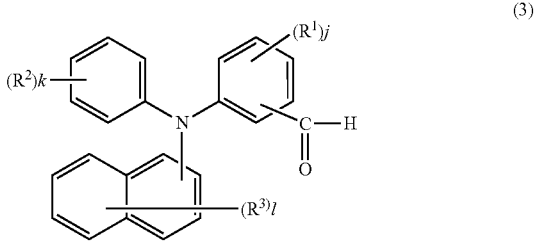

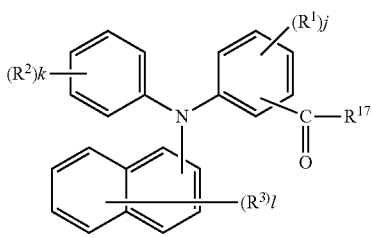

(3')

In the above general formulas (3) and (3'), $R^1$ to $R^3$, j, k and l are as defined in the general formula (1), and $R^{17}$ is an alkyl group having 1 to 6 carbon atoms, an aromatic hydrocarbon group, a condensed polycyclic aromatic group or an aromatic heterocyclic group.

Here, $R^{17}$ is a group corresponding to $R^4$ or $R^6$ (excluding, however, hydrogen atom) in the general formula (1a) that represents the group $X^1$.

Next, by utilizing the Wittig reaction, the carbonyl group (formyl group or ketone group) that is introduced is converted into the group $X^1$ represented by the general formula (1a) to thereby introduce the group $X^1$.

To obtain the carbonyl compound of the above general formula (3) by introducing the carbonyl group (formyl group) into the diphenylnaphthylamine compound of the general formula (2), the naphthylamine compound may be reacted with a formylating agent such as N,N-dimethylformamide or N-methylformanilide in the presence of a phosphorus oxychloride.

The reaction is, usually, conducted by using a solvent which is inert to the reaction, such as o-dichlorobenzene or benzene. Here, it is allowable to use the formylating agent in a very excess amount so as to also serve as a solvent for the reaction.

To obtain the carbonyl compound of the above general formula (3') by introducing the carbonyl group (ketone group) into the diphenylnaphthylamine compound, further, the naphthylamine compound may be reacted with an acid chloride ($R^{17}$COCl) in the presence of a Lewis acid such as aluminum chloride, iron chloride or zinc chloride. The reaction is, usually, conducted by using a solvent inert to the reaction, such as nitrobenzene, dichloromethane or carbon tetrachloride.

To convert the carbonyl group in the carbonyl compound of the above general formula (3) or (3') to the group $X^1$ by utilizing the Wittig reaction, further, the carbonyl compound may be reacted with a triphenylphosphine and with a halogen compound represented by the following general formula (4) or (4'),

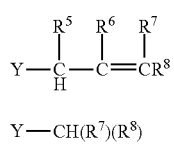

(4)

Y—CH($R^7$)($R^8$)  (4')

wherein,
$R^5$ to $R^8$ are the same as those of the general formula (1a), and
Y is a halogen atom such as chlorine atom or bromine atom.

Through the above reaction, the group $X^1$ is introduced into the diphenylnaphthylamine compound of the above general formula (2). Namely, a compound represented by the following general formula (5) is obtained.

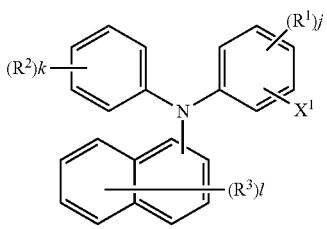

(5)

wherein,
$R^1$, $R^2$, $R^3$, j, k, l and $X^1$ are the same as those defined in the general formula (1).

That is, if a halogen compound of the general formula (4) (or a corresponding Wittig reagent) is used, then the value m of the group $X^1$ that is introduced is 1 and if a halogen compound of the general formula (4') (or a corresponding Wittig reagent) is used, then the value m of the group $X^1$ that is introduced is 0.

The above reaction (Wittig reaction) is conducted by using an organic solvent inert to the reaction, such as N,N-dimethylformamide, N,N-dimethylacetamide, tetrahydrofuran, dioxane, benzene or toluene.

Instead of using the halogen compound and the triphenylphosphine, it is also allowable to react the carbonyl compound of the above general formula (3) or (3') with a Wittig reagent obtained by acting a trialkoxyphosphorus compound upon the halogen compound.

It is desired that the temperature of the Wittig reaction is in a range of 10 to 200° C. and, specifically, 20 to 100° C.

Desirably, further, the Wittig reaction is conducted in the presence of a base catalyst such as n-butyllithium, phenyllithium, sodium methoxide, sodium ethoxide or potassium tert-butoxide.

(Introduction of the Group $X^2$)

To introduce the group $X^2$ into the compound of the general formula (5) in which the group $X^1$ has been introduced as described above, the carbonyl group (formyl group or ketone group) is introduced in the same manner as introducing the group $X^1$ to form a carbonyl compound and, next, the carbonyl group is converted into the group $X^2$ through the Wittig reaction.

That is, the formyl group or the ketone group is introduced into the compound of the general formula (5) in the same manner as described above to synthesize a compound represented by the following general formula (6),

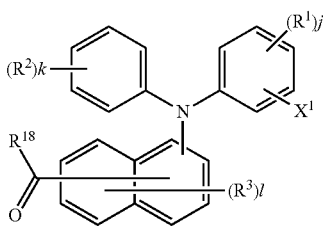

(6)

wherein, $R^1$, $R^2$, $R^3$, j, k, l and $X^1$ are the same as those defined in the general formula (1), and $R^{18}$ is a hydrogen atom, an alkyl group having 1 to 6 carbon atoms, an aromatic hydrocarbon group, a condensed polycyclic aromatic group or an aromatic heterocyclic group.

If formylation is conducted during the reaction, $R^{18}$ becomes a hydrogen atom and if a ketone is obtained by using the acid chloride ($R^{18}$COCl), $R^{18}$ becomes a group other than the hydrogen atom.

Here, the group $R^{18}$ is a group corresponding to $R^9$ or $R^{11}$ in the general formula (1b) that represents the group $X^2$.

Upon subjecting the carbonyl compound of the general formula (6) obtained as described above to the Wittig reaction in the same manner as when the group $X^1$ is introduced, it is allowed to obtain the diphenylnaphthylamine derivative of the present invention represented by the general formula (1), specifically, by the general formula (1') and, most desirably, by the general formula (1") or (1''').

The Wittig reaction uses a halogen compound represented by the following general formula (7) or (7'),

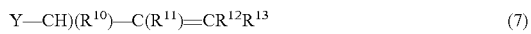

$$Y-CH(R^{10})-C(R^{11})=CR^{12}R^{13} \quad (7)$$

$$Y-CH(R^{12})(R^{13}) \quad (7')$$

wherein,

Y is a halogen atom such as chlorine atom or bromine atom, and $R^{10}$ to $R^{13}$ are as defined in the above general formula (1b), or uses a Wittig reagent derived from the above halogen compound (7) or (7') instead of using the halogen compound represented by the above general formula (4) or (4').

In introducing the group $X^1$ or $X^2$, the carbonyl group (formyl group) can be introduced by introducing a halogen atom into a benzene ring by the known halogenation reaction followed by the reaction with magnesium or lithium to obtain an organometal compound thereof, and reacting the organometal compound with an N,N-dimethylformamide.

The halogenation reaction has been closely described in, for example, The fourth series of Experimental Chemistry 19 (pp. 363-482, Japan Chemical Society, 1992), and the reaction of the organometal compounds with the dimethylformamide has been closely described in The fourth series of Experimental Chemistry 21 (pp. 23-44 and pp. 179-196, Japan Chemical Society, 1991).

The compound having a double bond newly formed by the Wittig reaction is obtained as a cis-form, a trans-form or a mixture of the cis-form and the trans-form. In the diphenylnaphthylamine derivatives of the invention, therefore, the double bond in the general formula (1a) or (1b) expresses any one of the cis-form, the trans-form or the mixture of the cis-form and the trans-form.

After the reaction, the refining is conducted by the adsorptive refining by using column chromatograph, silica gel, active carbon or active clay, or by the recrystallization or the crystallization using a solvent.

The obtained compound can be identified by the NMR measurement or by the elemental analysis.

The diphenylnaphthylamine derivatives of the invention thus obtained have a high charge mobility, and can be favorably used as a charge-transporting agent in the organic photosensitive materials for electrophotography. They can be, further, used as a material for the organic electroluminescent (EL) elements.

<Organic Photosensitive Materials for Electrophotography>

The organic photosensitive materials using the diphenylnaphthylamine derivative of the invention as the charge-transporting agent comprise a photosensitive layer that contains the charge-transporting agent and a charge-generating agent formed on an electrically conducting substrate, and can be classified into those in which the photosensitive layer is a single layer containing the charge-transporting agent and the charge-generating agent (single-layer type photosensitive layer) and those in which the photosensitive layer comprises a charge-transporting layer containing the charge-transporting agent and a charge-generating layer containing the charge-generating agent (lamination type photosensitive layer).

As the electrically conducting substrate for supporting the photosensitive layer, there can be used an electrically conducting material that has been used for the known photosensitive materials for electrophotography. Concretely, there can be used a sheet of a metal such as copper, aluminum, silver, iron, zinc or nickel or an alloy thereof, or a drum made of such a sheet. There can be, further, used a plastic film or a cylinder on which the above metal is vapor-deposited or electroplated, or a glass, a paper or a plastic film on which a layer of an electrically conducting compound such as electrically conducting polymer, indium oxide or tin oxide is applied or vapor-deposited.

The photosensitive layer is formed on the electrically conducting substrate by vapor deposition depending upon the type of the photosensitive layer (in the case of the lamination type photosensitive layer) but is, usually, formed by using a resin binder. Namely, the photosensitive layer of the single layer type or the lamination type is formed by dissolving the charge-transporting agent and the charge-generating agent in an organic solvent together with the resin binder to prepare a coating solution thereof, and applying the coating solution onto the electrically conducting substrate followed by drying.

As the resin binder used for forming the photosensitive layer, there can be used a thermoplastic or thermosetting resin that has heretofore been used for forming photosensitive layers. Concrete examples thereof include (meth)acrylic resins such as polyacrylate and polymethacrylate, as well as polyamide resin, acrylonitrile resin, vinyl chloride resin, acetal resin, butylal resin, vinyl acetate resin, polystyrene resin, polyolefin resin, cellulose ester, phenol resin, epoxy resin, polyester, alkyd resin, silicone resin, polycarbonate resin, polyurethane resin and polyimide resin. There can be further used such organic photoconductive polymers as polyvinylcarbazole, polyvinylanthracene and polyvinylpyrene as the resin binder.

The above resin binders are used in a single kind or in a combination of two or more kinds. In the invention, a polycarbonate resin is preferably used as the binder resin for the charge-transporting layer of the lamination type photosensitive layer and, specifically, a polycarbonate having a recurring unit represented by the following formula (A) is used,

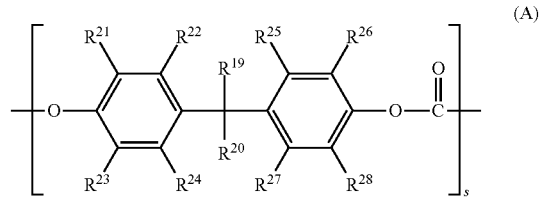

wherein, $R^{19}$ and $R^{20}$ may be the same or different, and are hydrogen atoms, alkyl groups having 1 to 4 carbon atoms, alkoxy groups having 1 to 4 carbon atoms or phenyl groups for which a halogen atom may be substituted, and may form a ring together, $R^{21}$ to $R^{28}$ may be the same or different, and are hydrogen atoms, halogen atoms, alkyl groups having 1 to 6 carbon atoms, alkoxy groups having 1 to 6 carbon atoms or phenyl groups, and s is a positive integer.

Among the polycarbonate resins having the recurring unit represented by the above formula (A), the following polycarbonate resins are preferred examples.

(1) A bisphenol A type polycarbonate resin (e.g., Eupilon E Series manufactured by MITSUBISHI GAS CHEMICAL COMPANY, INC.) having a recurring unit represented by the following formula (B),

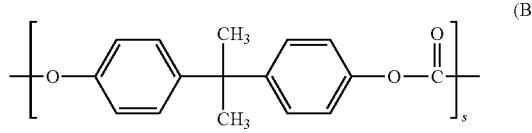

wherein, s is a positive integer.

(2) A bisphenol Z type polycarbonate resin (e.g., Eupilon Z Series manufactured by MITSUBISHI GAS CHEMICAL COMPANY, INC.) having a recurring unit represented by the following formula (C),

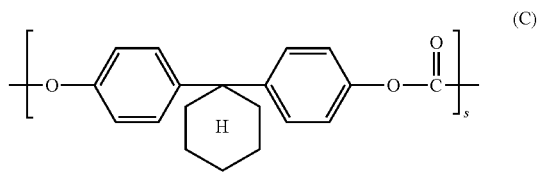

wherein, s is a positive integer.

(3) A copolymerized polycarbonate resin containing bisphenol A, bisphenol Z and biphenol as structural units.

The copolymerized polycarbonate resin has been disclosed in JP-A-4-179961, and is, for example, a bisphenol/biphenol type polycarbonate resin represented by the following formula (D),

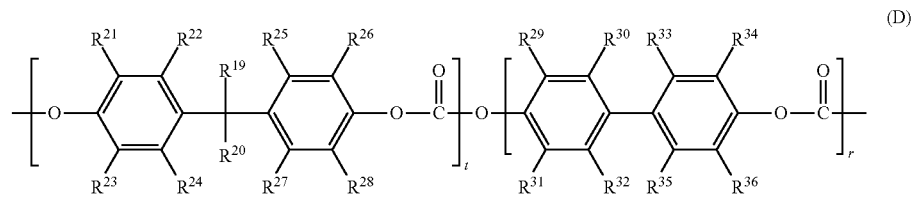

wherein, $R^{19}$ to $R^{28}$ are the same as $R^{19}$ to $R^{28}$ in the above formula (A), $R^{29}$ to $R^{36}$ may be the same or different, and are hydrogen atoms, halogen atoms, alkyl groups having 1 to 6 carbon atoms, alkoxy groups having 1 to 6 carbon atoms or phenyl groups, $R^{29}$ and $R^{30}$, $R^{31}$ and $R^{32}$, $R^{33}$ and $R^{34}$, and $R^{35}$ and $R^{36}$ together may form a ring, respectively, and t and r represent mole numbers of the above recurring units and are, preferably, the numbers satisfying $t/(t+r)=0.1$ to $0.9$.

Among the above copolymerized polycarbonate resins, a specifically preferred example is the bisphenol A/biphenol type polycarbonate resin represented by the following formula (E),

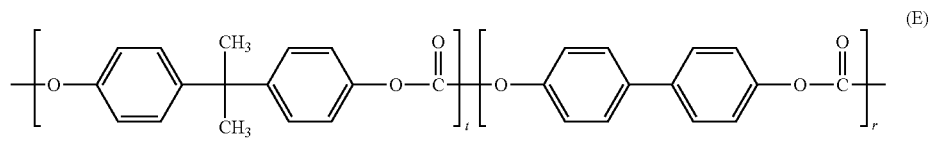

wherein, t and r represent mole numbers of the recurring units, and $t/(t+r)=0.85$.

In addition to the polycarbonate resins having the recurring unit of the above formula (A), there can be preferably used polycarbonate resins having recurring units of the following formulas (F) to (I).

(4) A polycarbonate resin having a recurring unit represented by the following formula (F),

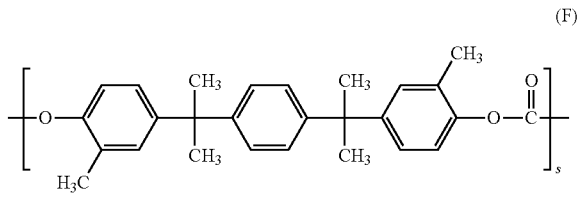

(F)

wherein, s is a positive integer.

The above copolymerized polycarbonate resin has been disclosed in JP-A-6-214412.

(5) A polycarbonate resin having a recurring unit represented by the following formula (G),

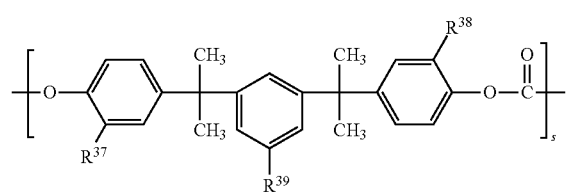

(G)

wherein, $R^{37}$, $R^{38}$ and $R^{39}$ may be the same or different, and are hydrogen atoms, halogen atoms, alkyl groups having 1 to 6 carbon atoms, cycloalkyl groups, aromatic hydrocarbon groups, condensed polycyclic aromatic groups or alkyl groups substituted with aromatic hydrocarbon group or condensed polycyclic aromatic group, and s is a positive integer.

The above copolymerized polycarbonate has been disclosed in, for example, JP-A-6-222581.

(6) A siloxane type polycarbonate resin having a recurring unit represented by the following formula (H)

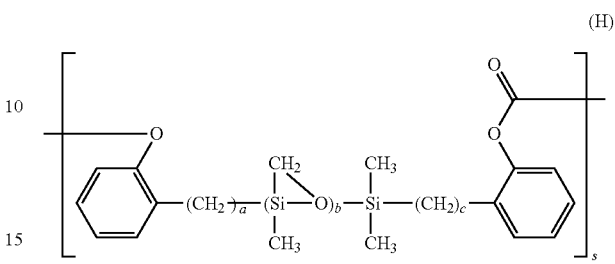

(H)

wherein, a, b, c and s are positive integers, or represented by the following formula (I),

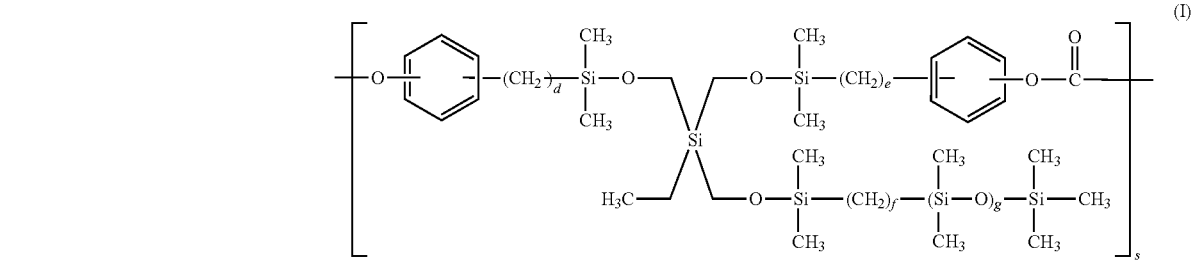

(I)

wherein, d, e, f, g and s are positive integers.

The above copolymerized polycarbonate resins have been disclosed in JP-A-5-088398 and JP-A-11-065136.

There is no specific limitation on the organic solvent used for the preparation of a coating solution for forming the photosensitive layer if it is capable of dissolving the charge-transporting agent (e.g., diphenylnaphthylamine derivative of the general formula (1)) added thereto or the resin binder and if it is capable of dissolving or dispersing the charge-generating agent. Usually, there can be used the following compounds in one kind or in a combination of two or more kinds.

Alcohols such as methanol, ethanol and 2-propanol;

ketones such as acetone, methyl ethyl ketone and cyclohexanone;

amides such as N,N-dimethylformamide and N,N-dimethylacetamide;

sulfoxides such as dimethyl sulfoxide;

ethers such as tetrahydrofurane, dioxane, dioxorane, ethylene glycol dimethyl ether, diethyl ether, diisopropyl ether and tert-butylmethyl ether;

esters such as ethyl acetate and methyl acetate;

aliphatic halogenated hydrocarbons such as methylene chloride, chloroform, 1,2-dichloroethane, dichloroethylene, carbon tetrachloride and trichloroethylene;

aromatic halogenated hydrocarbons such as chlorobenzene and dichlorobenzene;

aromatic hydrocarbons such as benzene, toluene and xylene; and aliphatic hydrocarbons such as pentane, hexane, heptane, octane and cyclohexane.

The coating solution that uses the above organic solvent is prepared by dissolving or dispersing the resin binder as well as the charge-transporting agent and the charge-generating agent in the organic solvent depending on the form of the photosensitive layer to be formed.

That is, if a photosensitive layer of the single-layer type is to be formed, the coating solution is prepared by adding the charge-transporting agent, charge-generating agent and resin binder into the organic solvent.

If a photosensitive layer of the lamination type is to be formed, there are prepared a coating solution for forming the charge-transporting layer by adding the charge-transporting agent and the resin binder into the organic solvent, and a coating solution for forming the charge-generating layer by adding the charge-generating agent and the resin binder to the organic solvent.

As required, further, various additives may be added to the above coating solutions in order to improve stability and applicability of the coating solutions, and charge characteristics and durability of the photosensitive layer.

As the additive, there can be exemplified plasticizers such as biphenylene compound, m-phenyl compound and dibutyl phthalate; surface lubricants such as silicone oil, grafted silicone polymer and fluorocarbons; potential stabilizers such as dicyanovinyl compound and carbazole derivatives; monophenol type antioxidants such as 2,6-di-tert-butyl-4-methylphenol; bisphenol type antioxidants; amine type antioxidants such as 4-diazabicyclo[2,2,2]octane; salicylic acid type antioxidants; antioxidants such as tocophenol; ultraviolet ray absorbers; and sensitizers.

These additives can be suitably used in amounts in a range in which they do not hinder the properties of the photosensitive layer or the applicability of the coating solution.

The above coating solution is applied by a method known per se., such as dip-coating method, spray-coating method, spinner-coating method, Meyer's bar-coating method, blade-coating method, roller-coating method or curtain-coating method.

The desired photosensitive layer is formed by drying the coating of the above coating solution. If the photosensitive layer of the lamination type is to be formed, the charge-generating layer or the charge-transporting layer is formed on the electrically conducting substrate, and the charge-transporting layer or the charge-generating layer is formed thereon.

The above drying is preferably conducted by maintaining the coating at room temperature followed by heating. The heating is conducted at a temperature of 30 to 200° C. for a period of 5 minutes to 2 hours in a windless state or by blowing the air.

Prior to forming the photosensitive layer, an underlying layer may be formed on the electrically conducting substrate, and the photosensitive layer may be formed on the underlying layer.

The underlying layer is for improving the barrier function for preventing deterioration on the surface of the electrically conducting substrate and for improving close adhesion between the photosensitive layer and the surface of the electrically conducting substrate, and is formed by using a thin resin layer such as polyvinyl alcohol, nitrocellulose, casein, ethylene/acrylic acid copolymer or polyamide such as nylon or polyurethane, or gelatin, by using an aluminum oxide layer or by using a resin layer in which a metal oxide such as titanium oxide is dispersed.

It is desired that the underlying layer has a thickness in a range of 0.1 to 5 μm and, specifically, 0.5 to 3 μm. This is because if the underlying layer is too thick, inconvenience arouses, such as an increase in the residual potential in the photosensitive material due to an increase in the resistivity.

On the photosensitive layer thus formed, it is also allowable to suitably form a protection layer for preventing the photosensitive layer from being deteriorated by ozone or nitrogen oxide and for preventing the wear of the photosensitive layer.

In the present invention as described above, the diphenylnaphthylamine derivative of the general formula (1) is used as the charge-transporting agent in the photosensitive layer that is formed as described above. The naphthylamine derivative is used in an amount that may differ depending upon the kind of the photosensitive layer that is formed but is used, usually, in a range of 10 to 1,000 parts by weight, preferably, 30 to 500 parts by weight and, more preferably, 40 to 200 parts by weight per 100 parts by weight of the resin binder, and is made present in the single-layer type photosensitive layer or in the charge-transporting layer of the photosensitive layer of the lamination type.

As required, further, the above photosensitive layer may, further, use other charge-transporting agents than the above diphenylnaphthylamine derivative in amounts in a range in which they do not impair excellent properties of the naphthylamine derivative.

The other charge-transporting agents are the ones that have been known per se., and the following compounds are representative examples.

Other charge-transporting agents;

(1) Hydrazone compounds represented by the following general formula (8),

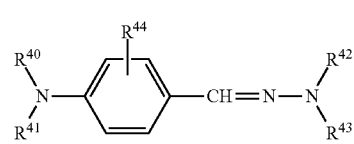

(8)

wherein, $R^{40}$ and $R^{41}$ may be the same or different, and are lower alkyl groups having 1 to 4 carbon atoms, aromatic hydrocarbon groups, condensed polycyclic aromatic groups or aralkyl groups, $R^{42}$ and $R^{43}$ may be the same or different, and are lower alkyl groups having 1 to 4 carbon atoms, aromatic hydrocarbon groups, condensed polycyclic aromatic groups, aralkyl groups or heterocyclic groups, and $R^{42}$ and $R^{43}$ together may form a ring, and $R^{44}$ is a hydrogen atom, a lower alkyl group having 1 to 4 carbon atoms, an aromatic hydrocarbon group, a condensed polycyclic aromatic group, an aralkyl group, a lower alkoxy group having 1 to 4 carbon atoms or a halogen atom, and $R^{44}$ and $R^{40}$ or $R^{41}$ together may form a ring.

The above hydrazone compounds have been disclosed, for example, in JP-B-55-042380 (patent document 6), and JP-A-61-023154 (patent document 11).

(2) Triphenylamine dimers represented by the following general formula (9),

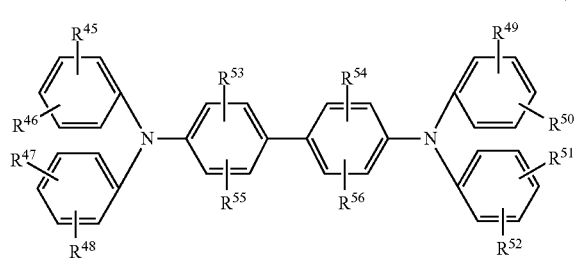

wherein,
R$^{45}$ to R$^{56}$ may be the same or different, and are hydrogen atoms, lower alkyl groups having 1 to 4 carbon atoms, lower alkoxy groups having 1 to 4 carbon atoms, halogenoalkyl groups having 1 to 4 carbon atoms, halogenoalkoxy groups having 1 to 4 carbon atoms, aromatic hydrocarbon groups, condensed polycyclic aromatic groups or halogen atoms.

The above triphenylamine dimers have been disclosed in, for example, JP-B-58-032372 (patent document 12).

(3) Distyryl compounds represented by the following general formula (10),

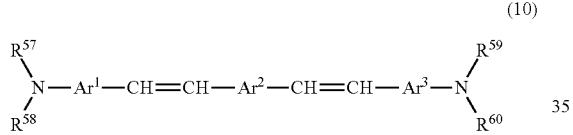

wherein,
R$^{57}$ to R$^{60}$ may be the same or different, and are lower alkyl groups having 1 to 4 carbon atoms, aromatic hydrocarbon groups or condensed polycyclic aromatic groups, Ar$^1$ and Ar$^3$ may be the same or different, and are phenylene groups, Ar$^2$ is a divalent group of a monocyclic or polycyclic aromatic hydrocarbon having 4 to 14 carbon atoms, or a divalent group of a monocyclic or polycyclic aromatic heterocyclic ring having 4 to 14 carbon atoms, and
the substituent which Ar$^1$, Ar$^2$ or Ar$^3$ may possess is a group selected from the lower alkyl group having 1 to 4 carbon atoms, lower alkoxy group having 1 to 4 carbon atoms, aryloxy group and halogen atom.

The above distyryl compounds have been disclosed in, for example, U.S. Pat. No. 3,873,312 (patent document 13).

(4) As the compounds other than the above compounds, there can be exemplified tetraphenylbutadiene compounds, α-phenylstilbene compounds, polyvinylcarbazole compounds and triphenylmethane compounds.

The charge-generating agents added into the photosensitive layer are the materials that absorb light and generate an electric charge at a high efficiency, and can be roughly divided into the inorganic charge-generating agents and the organic charge-generating agents.

As the inorganic charge-generating agents, there have been known selenium, selenium-tellurium, amorphous silicon and the like.

As the organic charge-generating agents, there have been known cationic dyes (e.g., thiapyrylium salt dyes, azulenium salt dyes, thiacyanine dyes, quinocyanine dyes), squalium salt pigments, phthalocyanine pigments, polycyclic quinone pigments (e.g., anthanthrone pigments, dibenzpyrenequinone pigments, pyranthrone pigments), indigo pigments, quinacrydone pigments, azo pigments, pyrrolopyrrole pigments and perylene pigments.

In the invention, the above inorganic charge-generating agents and the organic charge-generating agents can be each used in a single kind or in a combination of two or more kinds, and the organic charge-generating agents are specifically preferably used.

Among the organic charge-generating agents, there are specifically preferably used phthalocyanine pigments, azo pigments, perylene pigments and polycyclic quinone pigments, and described below are their concrete examples.

Concrete examples of the phthalocyanine pigment include alkoxytitanium phthalocyanine (Ti(OR)$_2$Pc), oxotitanium phthalocyanine (TiOPc), copper phthalocyanine (CuPc), metal-free phthalocyanine (H$_2$Pc), hydroxygallium phthalocyanine (HOGaPc), vanadyl phthalocyanine (VOPc) and chloroindium phthalocyanine (ClInPc). More closely, as the TiOPc, there can be exemplified α-TiOPc, β-TiOPc, γ-TiOPc, m-TiOPc, Y-TiOPc, A-TiOPc, B-TiOPc and TiOPc amorphous and as the H$_2$Pc, there can be exemplified α-H$_2$Pc, β-H$_2$Pc, τ-H$_2$Pc and x-H$_2$Pc.

As the azo pigment, there can be exemplified monoazo compounds, bisazo compounds and trisazo compounds. However, particularly preferred are the bisazo compounds represented by the following structural formulas (J) to (L) and the trisazo compounds represented by the following structural formula (M).

Bisazo compounds of the structural formula (J),

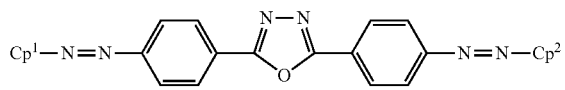

wherein Cp$^1$ and Cp$^2$ may be the same or different, and are the groups represented by the following formula (11) or (12),

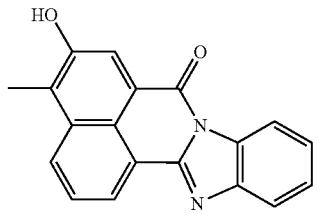

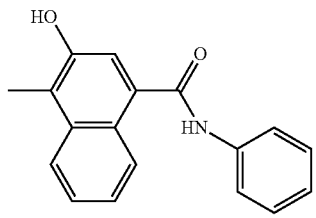

Bisazo compounds of the structural formula (K),

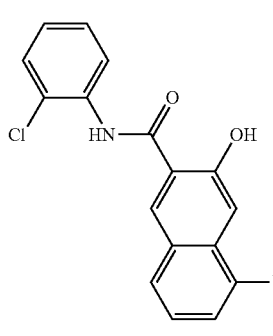
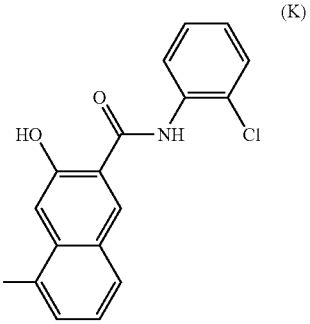

(K)

Bisazo compounds of the structural formula (L),

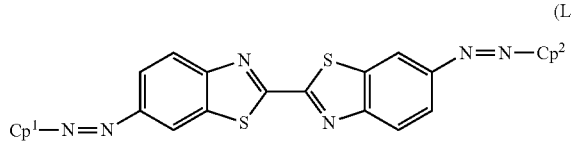

(L)

wherein $Cp^1$ and $Cp^2$ may be the same or different, and are the groups represented by the above formula (11) or (12).

Trisazo compounds of the structural formula (M),

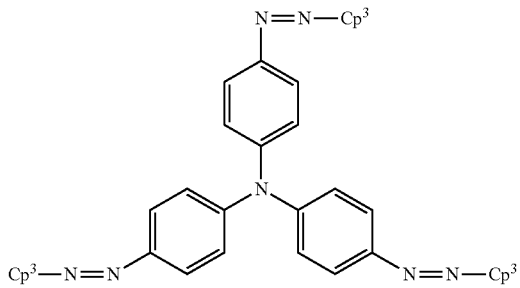

(M)

wherein $Cp^3$ is a group represented by the following structural formula (13),

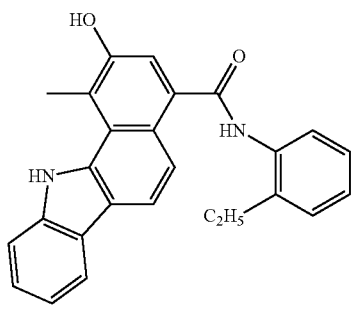

(13)

As the perylene compounds and polycyclic quinone pigments, further, the compounds represented by the following structural formulas (N) and (O) are particularly preferred.

Structural formula (N);

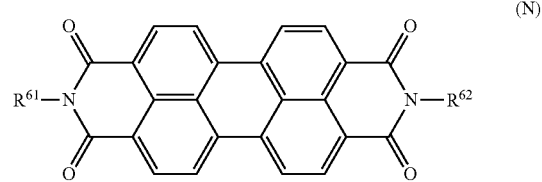

(N)

wherein $R^{61}$ and $R^{62}$ may be the same or different, and are lower alkyl groups having 1 to 4 carbon atoms, aromatic hydrocarbon groups or condensed polycyclic aromatic groups.

Structural formula (O);

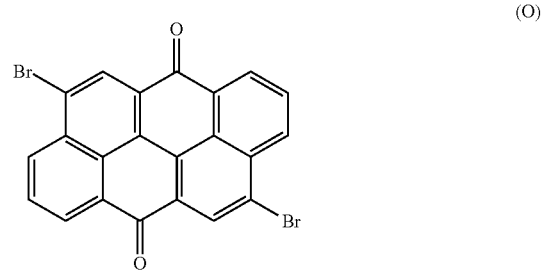 [SMILES: O=c1c2cc(Br)c3cccc4c(=O)c5cc(Br)c6cccc1c6c5-c2c34]

(O)

The ratio of the charge-generating agent occupying the photosensitive layer may differ depending on the type of the photosensitive layer. In the single-layer type photosensitive layer, in general, the ratio of the charge-generating agent is 0.2 to 40 parts by mass and, specifically, 0.5 to 20 parts by mass per 100 parts by mass of the resin binder. In the charge-generating layer of the lamination type photosensitive layer, the ratio of the charge-generating agent is, generally, 30 to 400 parts by mass and, specifically, 60 to 300 parts by mass per 100 parts by mass of the resin binder.

In the case of the single-layer type photosensitive layer, the photosensitive layer has a thickness of about 5 to about 100 μm and, specifically, about 15 to about 45 μm.

In the case of the lamination type photosensitive layer, it is desired that the charge-generating layer has a thickness of about 0.01 to about 5 μm and, specifically, about 0.05 to about 2 μm, and the charge-transporting layer has a thickness of about 5 to about 40 μm and, specifically, about 10 to about 30 μm.

Upon being electrically connected to the charge-generating layer, the charge-transporting layer in the lamination type photosensitive layer can have a function for receiving the charge carrier injected from the charge-generating layer and transferring the charge carrier to the surface of the photosensitive layer in the presence of an electric field. Here, the charge-transporting layer may be laminated on or under the charge-generating layer. It is, however, desired that the charge-transporting layer is laminated on the charge-generating layer from the standpoint of suppressing the charge-generating layer from being deteriorated.

The organic photosensitive material for electrophotography has the photosensitive layer which contains the diphenyl-naphthylamine derivative of the above general formula (1) as the charge-transporting agent, and effectively avoids the precipitation of crystals or the formation of pinholes at the time of forming the photosensitive layer owing to the excellent properties of the naphthylamine derivative, and is, further, highly sensitive developing a low residual potential and is capable of forming vivid images over extended periods of time even after the images are repetitively formed by electrophotography.

The image is formed by using the above organic photosensitive material based on the electrophotography through a process of, for example, electrically charging the surface of the photosensitive material into a predetermined polarity by using a corona charger, forming an electrostatic latent image by the irradiation with light (exposure to image-bearing light) according to the image data, developing the electrostatic latent image by using a known developing agent, forming a toner image on the surface of the photosensitive material, transferring the toner image onto a predetermined recording material, and fixing the transferred toner image on the recording material by the application of heat and pressure. The surface of the photosensitive material after the toner image has been transferred thereon is irradiated with charge-removing light to remove the electric charge. Further, the toner remaining thereon is removed by using a cleaning blade or the like, and the photosensitive material is put to the next image-forming process.

EXAMPLES

Examples of the invention will now be concretely described to which only, however, the invention is in no way limited.

Synthesis Example 1

Synthesis of an Example Compound 25

A compound represented by the following structural formula (14) (see patent document 14) was prepared as a starting material.

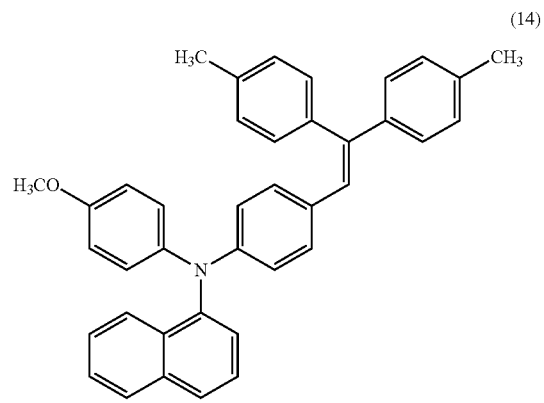 [SMILES: COc1ccc(N(c2ccc(C=C(c3ccc(C)cc3)c3ccc(C)cc3)cc2)c2cccc3ccccc23)cc1]

(14)

5.3 Grams of the above compound and 21.2 g of an N,N-dimethylformamide were introduced into a reaction container, and to which 15.3 g of a phosphoryl trichloride was added dropwise. The mixture was stirred being heated at 80° C. for 3 hours, left to cool, and to which 100 g of water was added dropwise in a manner of being cooled, followed by the addition of the sodium carbonate to render the reaction solution to be alkaline.

Next, the reaction solution was heated at 60° C. for 3 hours and was, thereafter, extracted with toluene. After washed with water and, then, with saturated brine, the solution was dried by using the magnesium sulfate. After that, the solvent was distilled off to obtain 5.1 g of a yellow solid formyl compound represented by the following structural formula (15),

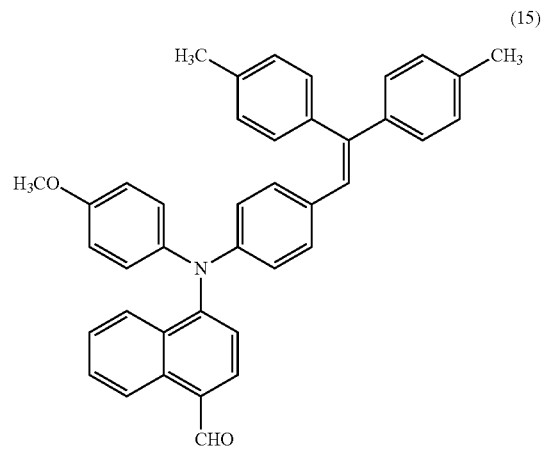 [SMILES: COc1ccc(N(c2ccc(C=C(c3ccc(C)cc3)c3ccc(C)cc3)cc2)c2ccc(C=O)c3ccccc23)cc1]

(15)

5 Grams of the obtained formyl compound and 3 g of a diphenylmethyldiethyl phosphorous ester were dissolved in 20 ml of an N,N-dimethylformamide, and to which 0.4 g of a sodium methylato was added while maintaining the temperature at 20±5° C. After stirred for 2 hours, 20 ml of ion-exchanged water was added thereto, and the refining was conducted in a customary manner to obtain 5.8 g of a yellow solid matter (yield, 82%).

The obtained yellow solid matter was identified for its structure by the elemental analysis and by the NMR measurement. FIG. 1 shows an NMR spectrum.

The values of elemental analysis were as follows:

|  | Carbon | Hydrogen | Nitrogen | Oxygen |
|---|---|---|---|---|
| Measured (%) | 89.70% | 6.15% | 1.92% | 2.23% |
| Calculated (%) | 89.67% | 6.11% | 1.97% | 2.25% |

From the above results, it was learned that the obtained yellow solid matter corresponded to the above Example compound 25 and was a compound represented by the following formula.

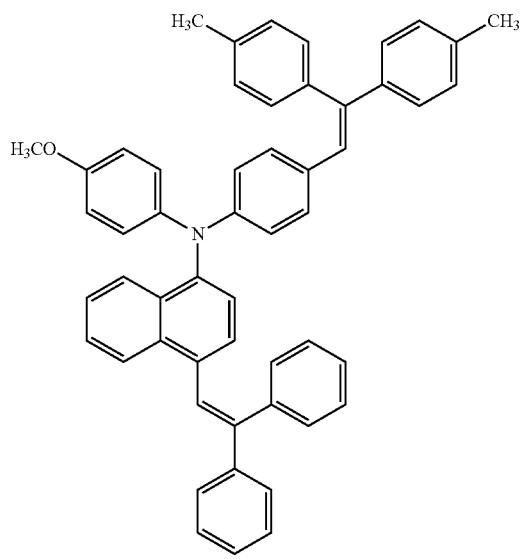 [SMILES: COc1ccc(N(c2ccc(C=C(c3ccc(C)cc3)c3ccc(C)cc3)cc2)c2ccc(C=C(c3ccccc3)c3ccccc3)c3ccccc23)cc1]

Synthesis Example 2

Synthesis of an Example Compound 26

5 Grams of the formyl compound represented by the above structural formula (15) obtained in Example 1 and 3.3 g of a di-p-tolylmethyldiethyl phosphorous ester were dissolved in 20 ml of the N,N-dimethylformamide, and to which 0.4 g of the sodium methylato was added while maintaining the temperature at 20±5° C. After stirred for 2 hours, 20 ml of ion-exchanged water was added thereto, and the refining was conducted in a customary manner to obtain 4.8 g of a yellow solid matter (yield, 65%).

Figure 2:
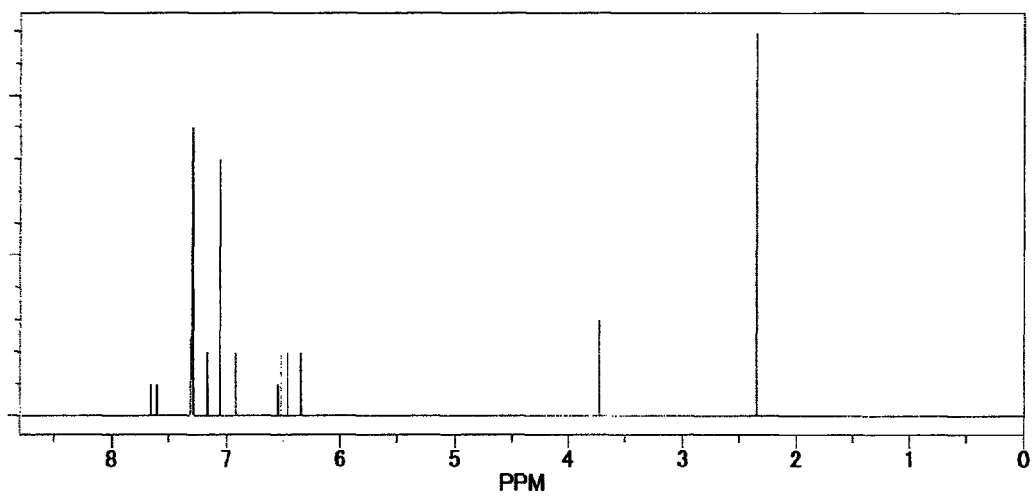
[FIG. 2] shows an NMR spectrum of a compound of Example 2 (Example Compound 26).

The obtained yellow solid matter was identified for its structure by the elemental analysis and by the NMR measurement. FIG. 2 shows an NMR spectrum.

The values of elemental analysis were as follows:

|  | Carbon | Hydrogen | Nitrogen | Oxygen |
|---|---|---|---|---|
| Measured (%) | 89.54% | 6.44% | 1.87% | 2.14% |
| Calculated (%) | 89.51% | 6.42% | 1.90% | 2.17% |

From the above results, it was learned that the obtained yellow solid matter corresponded to the above Example compound 26 and was a compound represented by the following formula.

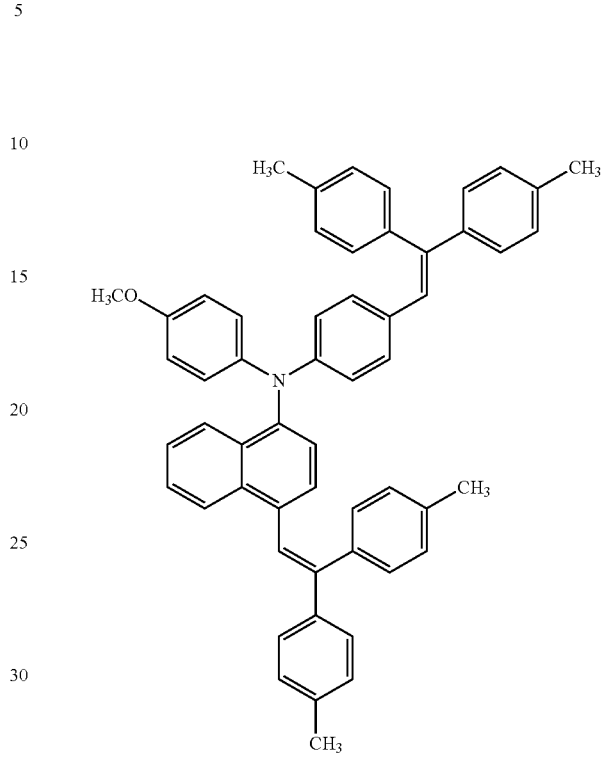

Synthesis Example 3

Synthesis of Example Compound 27

5.1 Grams of the formyl compound represented by the above structural formula (15) obtained in Example 1 and 3.3 g of a 3,3-diphenyl-2-propenyldiethyl phosphorous ester were dissolved in 20 ml of the N,N-dimethylformamide, and to which 0.4 g of the sodium methylato was added while maintaining the temperature at 20±5° C. After stirred for 2 hours, 20 ml of ion-exchanged water was added thereto, and the mixture was stirred being at 40° C. for 3 hours, and the refining was conducted in a customary manner to obtain 5.5 g of a yellow solid matter (yield, 75%).

Figure 3:
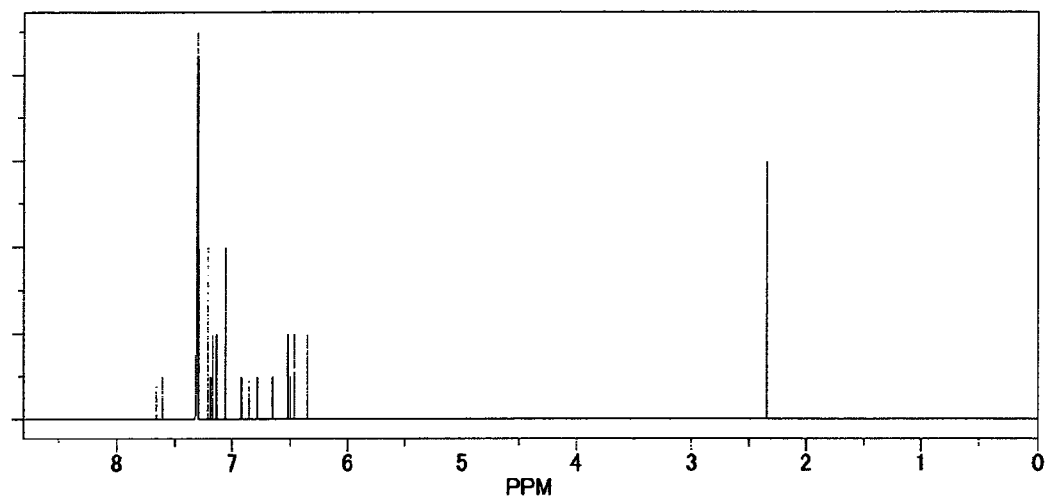
[FIG. 3] shows an NMR spectrum of a compound of Example 3 (Example Compound 27)

The obtained yellow solid matter was identified for its structure by the elemental analysis and by the NMR measurement. FIG. 3 shows an NMR spectrum.

The values of elemental analysis were as follows:

|  | Carbon | Hydrogen | Nitrogen | Oxygen |
|---|---|---|---|---|
| Measured (%) | 89.79% | 6.19% | 1.87% | 2.15% |
| Calculated (%) | 89.76% | 6.16% | 1.90% | 2.17% |

From the above results, it was learned that the obtained yellow solid matter corresponded to the above Example compound 27 and was a compound represented by the following formula.

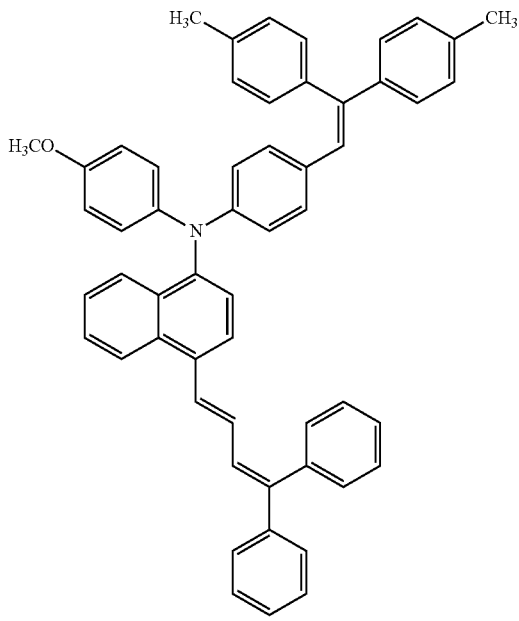 [SMILES: COc1ccc(N(c2ccc(C=C(c3ccc(C)cc3)c3ccc(C)cc3)cc2)c2ccc(/C=C/C=C(c3ccccc3)c3ccccc3)c3ccccc23)cc1]

Photosensitive Material Example 1

One part by mass of an alcohol-soluble polyamide (Amilan CM-4000 manufactured by Toray Industries, Inc.) was dissolved in 13 parts by mass of methanol. 5 Parts by mass of a titanium oxide (TIPAQUE CR-EL manufactured by ISHIHARA SANGYO KAISHA, LTD.) was added thereto and was dispersed by using a paint shaker for 8 hours to prepare a coating solution for forming under-coating layer. By using a wire bar, the coating solution was applied onto an aluminum surface of an aluminum-deposited PET film and was dried under normal pressure at 60° C. for one hour to form an under-coating layer of a thickness of 1 μm.

As a charge-generating material, there was provided the following titanyl phthalocyanine (charge-generating agent No. 1) having intense peaks at the diffraction angles 2θ±0.2° of 9.6, 24.1 and 27.2 in the X-ray diffraction spectrum of Cu—Kα, (Charge-generating agent No. 1)

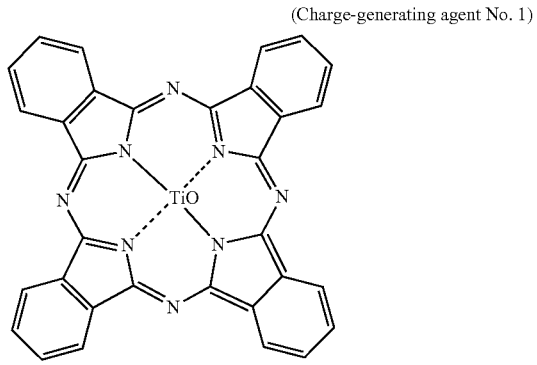

As the binder resin for forming the charge-generating layer, there was provided a polyvinyl butyral resin (S-LEC BL-S manufactured by SEKISUI CHEMICAL CO., LTD.).

1.5 Parts by mass of the above charge-generating agent was added into 50 parts by mass of a cyclohexanone solution containing 3% of the polyvinyl butyral resin, and was dispersed therein by using an ultrasonic stirrer for one hour.

By using the wire bar, the obtained dispersion solution was applied onto the under-coating layer, and was dried under normal pressure at 110° C. for one hour to form a charge-generating layer of a thickness of 0.6 μm.

As the binder resin for forming the charge-transporting layer, on the other hand, there was provided a polycarbonate resin (Eupilon Z manufactured by Mitsubishi Engineering Plastic Co.).

1.5 Part by mass of the diphenylnaphthylamine derivative (Example compound 25) synthesized in Example 1 was added as the charge-transporting agent to 18.75 parts by mass of a dichloroethane solution containing 8.0% of the polycarbonate resin, and was completely dissolved therein by applying ultrasonic waves thereto.

By using the wire bar, the solution was applied onto the charge-generating layer, and was dried under normal pressure at 110° C. for 30 minutes to form a charge-transporting layer of a thickness of 20 μm to thereby prepare a photosensitive material No. 1.

Photosensitive Material Examples 2 and 3

Photosensitive materials Nos. 2 and 3 were prepared by the same method as that of the Photosensitive Material Example 1 but using the diphenylnaphthylamine derivatives (Example compounds 26 and 27) synthesized in Examples 2 and 3 instead of using the charge-transporting agent used in the Photosensitive Material Example 1.

Photosensitive Material Comparative Example 1

For comparison, a photosensitive material No. 4 was prepared in the same manner as in the Photosensitive Material Example 1 but using a compound (Comparative compound No. 1) represented by the following structural formula instead of using the charge-transporting agent used in the Photosensitive Material Example 1.

(Comparative compound No. 1)

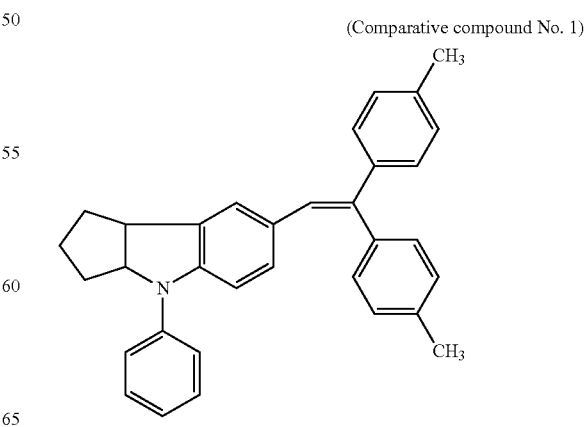

(Evaluating the Electrophotographic Properties of the Photosensitive Materials)

The photosensitive materials prepared in the Photosensitive Material Examples 1 to 3 and Photosensitive Material Comparative Example 1 were evaluated for their electrophotographic properties by using an electrostatic copy paper testing device (trade name "EPA-8100A").

First, the photosensitive material was corona-charged at −5.5 kV in a dark place, and a charged potential VO at this moment was measured.

Next, the photosensitive material was exposed to the 780 nm monochromatic light of 1.0 μW/cm$^2$ to find a half-value exposure E1/2 (μJ/cm$^2$) and a residual potential Vr (−V) after exposed to light for 2 seconds. The results were as shown in Table 1.

TABLE 1

| Example, Comp. Example | Photosensitive material No. | Charged potential VO (−V) | Half-value exposure E1/2 (μJ/cm$^2$) | Residual potential Vr (−V) |
| --- | --- | --- | --- | --- |
| Photosensitive material Ex. 1 | 1 | 759 | 0.25 | 32 |
| Photosensitive material Ex. 2 | 2 | 755 | 0.25 | 30 |
| Photosensitive material Ex. 3 | 3 | 751 | 0.25 | 28 |
| Photosensitive material Comp. Ex. 1 | 4 | 775 | 0.26 | 40 |

It will be learned from the above results, that low residual potentials are possessed by the photosensitive materials for electrophotography having a photosensitive layer that contains the diphenylnaphthylamine derivative of the present invention as the charge-transporting agent.

Photosensitive Material Example 4

As a charge-generating material, there was provided a titanyl phthalocyanine (charge-generating agent No. 2) having intense peaks at the diffraction angles 2θ±0.2° of 7.5, 10.3, 12.6, 22.5, 24.3, 25.4 and 28.6 in the X-ray diffraction spectrum of Cu—Kα.

A charge-generating layer having a thickness of 0.2 μm was formed on the aluminum surface of the aluminum-deposited PET film in quite the same manner as in the Photosensitive Material Example 1 but using the above charge-generating agent.

On the other hand, 0.9 parts by mass of the diphenylnaphthylamine derivative of Example 1 (Example compound 25) was added into 7.38 parts by mass of a tetrahydrofurane solvent containing 12.2% of the above polycarbonate resin, and was completely dissolved therein by applying ultrasonic waves thereto.

By using the wire bar, the solution was applied onto the above charge-generating layer and was dried under normal pressure at 110° C. for 30 minutes to form a charge-transporting layer of a thickness of 10 μm. Thereafter, a translucent metal electrode was vapor-deposited on the charge-transporting layer to prepare a photosensitive material No. 5.

Photosensitive Material Examples 5 and 6

Photosensitive materials Nos. 6 and 7 were prepared in the same manner as in the Photosensitive Material Example 4 but using the diphenylnaphthylamine derivatives (Example compounds 26 and 27) of Examples 2 and 3 instead of using the charge-transporting agent used in the Photosensitive Material Example 4.

Photosensitive Material Comparative Example 2

For comparison, a photosensitive material No. 8 was prepared in the same manner as in the Photosensitive Material Example 4 but using the Comparative compound No. 1 used in the Photosensitive Material Comparative Example 1 instead of using the charge-transporting agent used in the Photosensitive Material Example 4.

[Drift Mobility]

The photosensitive materials prepared in the Photosensitive Material Examples 4 to 6 and Photosensitive Material Comparative Example 2 were measured for their drift mobilities. The measurement was based on the time-of-flight method and was taken at 2×10$^5$ V/cm. The results were as shown in Table 2.

TABLE 2

| Example, Comp. Example | Photosensitive material No. | Drift mobility [cm$^2$/V · s] |
| --- | --- | --- |
| Photosensitive material Ex. 4 | 5 | 2.4 × 10$^{-5}$ |
| Photosensitive material Ex. 5 | 6 | 2.7 × 10$^{-5}$ |
| Photosensitive material Ex. 6 | 7 | 4.3 × 10$^{-5}$ |
| Photosensitive material Comp. Ex. 2 | 8 | 6.4 × 10$^{-6}$ |

It will be learned from the above results that the diphenylnaphthylamine derivatives of the present invention have high carrier mobilities.

INDUSTRIAL APPLICABILITY

The diphenylnaphthylamine derivatives of the present invention have high carrier mobilities, exhibit excellent properties as a charge-transporting agent, are very useful as a charge-transporting agent for forming the photosensitive layer in the organic photosensitive material for electrophotography, and provide an organic photosensitive material for electrophotography having such favorable properties as high sensitivity and low residual potential.

The invention claimed is:

1. An organic photosensitive layer formed on an electrically conductive substrate, wherein said organic photosensitive layer contains a diphenylnaphthylamine derivative as a charge-transporting agent, wherein the diphenylnaphthylamine derivative is represented by formula (1'''),

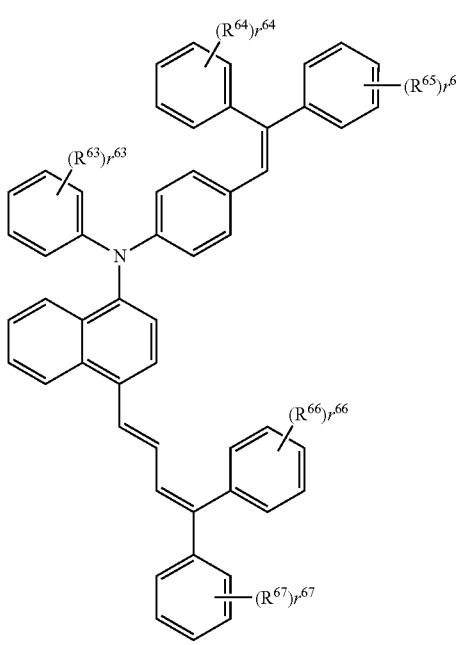

wherein,
$r^{63}$ to $r^{67}$ may be the same or different, and are integers of 0 to 5, $R^{63}$ to $R^{67}$ may be the same or different, and are groups selected from the group consisting of alkyl group having 1 to 6 carbon atoms, alkoxy group having 1 to 6 carbon atoms, halogen atom, aromatic hydrocarbon group, condensed polycyclic aromatic group, aromatic heterocyclic group, and disubstituted amino group having, as substituents, alkyl groups having 1 to 6 carbon atoms, alkenyl groups having 2 to 6 carbon atoms, aralkyl groups, aromatic hydrocarbon groups or aromatic heterocyclic groups, and when $R^{63}$, $R^{64}$, $R^{65}$, $R^{66}$ and $R^{67}$ are present in plural numbers, the plurality of $R^{63}$, $R^{64}$, $R^{65}$, $R^{66}$ and $R^{67}$ may be each the same or different, and may be bonded together to form a ring structure.

2. The organic photosensitive layer according to claim 1, which is used for electrophotography.

3. The organic photosensitive layer according to claim 2, wherein said organic photosensitive layer is a lamination type photosensitive layer comprising a charge-generating layer that contains a charge-generating agent dispersed in a resin binder and a charge-transporting layer that contains the charge-transporting agent dispersed in a resin binder.

4. The organic photosensitive layer according to claim 2, wherein said organic photosensitive layer is a single photosensitive layer containing a charge-generating agent and the charge-transporting agent dispersed in a resin binder.

* * * * *